(12) United States Patent
Harbeson

(10) Patent No.: US 8,592,487 B2
(45) Date of Patent: Nov. 26, 2013

(54) DEUTERATED DARUNAVIR

(75) Inventor: Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 438 days.

(21) Appl. No.: 12/387,327

(22) Filed: Apr. 28, 2009

(65) Prior Publication Data

US 2010/0113589 A1   May 6, 2010

Related U.S. Application Data

(63) Continuation-in-part of application No. 12/290,004, filed on Oct. 24, 2008.

(60) Provisional application No. 61/000,498, filed on Oct. 26, 2007.

(51) Int. Cl.
*A61K 31/34* (2006.01)
*A01N 43/08* (2006.01)
*C07D 493/00* (2006.01)
*C01B 4/00* (2006.01)

(52) U.S. Cl.
USPC ........... 514/709; 549/464; 514/885; 514/470; 423/647.7

(58) Field of Classification Search
USPC ......... 514/470, 709, 885; 549/464; 423/647.7
See application file for complete search history.

(56) References Cited

U.S. PATENT DOCUMENTS

| 5,843,946 | A | 12/1998 | Vazquez et al. |
|---|---|---|---|
| 6,221,335 | B1 | 4/2001 | Foster |
| 6,248,775 | B1 | 6/2001 | Vazquez et al. |
| 6,335,460 | B1 | 1/2002 | Vazquez et al. |
| 6,417,387 | B1 | 7/2002 | Vazquez et al. |
| 6,440,710 | B1 | 8/2002 | Keinan et al. |
| 6,472,407 | B1 | 10/2002 | Vazquez et al. |
| 6,603,008 | B1 | 8/2003 | Ando et al. |
| 6,924,286 | B1 | 8/2005 | Vazquez et al. |
| 7,141,609 | B2 | 11/2006 | Vazquez et al. |
| 7,517,990 | B2 | 4/2009 | Ito et al. |
| 2005/0261507 | A1 | 11/2005 | Doan et al. |
| 2005/0267074 | A1 | 12/2005 | Eissenstat et al. |
| 2006/0148865 | A1 | 7/2006 | Martin et al. |
| 2007/0060642 | A1 | 3/2007 | Goyvaerts et al. |
| 2007/0082929 | A1 | 4/2007 | Gant et al. |
| 2007/0197695 | A1 | 8/2007 | Potyen et al. |
| 2007/0248624 | A1* | 10/2007 | Tahri et al. ................ 424/208.1 |
| 2008/0103122 | A1 | 5/2008 | Veltri |
| 2008/0194554 | A1 | 8/2008 | McLean et al. |
| 2009/0076138 | A1* | 3/2009 | Czarnik ........................ 514/469 |
| 2009/0131363 | A1* | 5/2009 | Harbeson ...................... 514/45 |
| 2010/0305173 | A1 | 12/2010 | Harbeson et al. |
| 2011/0257111 | A1 | 10/2011 | Harbeson et al. |

FOREIGN PATENT DOCUMENTS

| WO | WO 94/04492 | 3/1994 |
|---|---|---|
| WO | WO 95/06030 | 3/1995 |
| WO | WO 95/26325 A2 | 10/1995 |
| WO | WO 99/65870 A2 | 12/1999 |
| WO | WO 00/76961 A1 | 12/2000 |
| WO | WO 03/022853 A1 | 3/2003 |
| WO | WO 2005/027855 A2 | 3/2005 |
| WO | WO 2005/063770 A1 | 7/2005 |
| WO | WO 2005/110428 A2 | 11/2005 |
| WO | WO 2007/118651 A1 | 10/2007 |
| WO | WO 2008/013834 A1 | 1/2008 |
| WO | WO 2009/055006 A1 | 4/2009 |
| WO | WO 2010/047819 A1 | 4/2010 |
| WO | WO 2010/127272 A2 | 11/2010 |

OTHER PUBLICATIONS

D.J. Kushner, et al, Pharmacological Uses and Perspectives of Heavy Water and Deuterated Compounds, 77 Can. J Physiol. Pharmacol. 79 (1999).*
Bachir Latli, et al, Synthesis of Deuterium-, Tritium-, and Carbon-14—labeled BILN2061, a Potent Hepatitis C Virus Protease Inhibitor, 48 J Label. Compd. Radiopharm., 447 (2005).*
Victor Ekhato, et al, Isotope Labeled 'HEA Moiety' in the Synthesis of Labeled HIV-Protease Inhibitors—Part I, 47 J Label. Compd. Radiopharm., 821 (2004).*
Victor Ekhato, et al, Isotope Labeled 'HEA/HEE' Moiety in the Synthesis of Labeled HIV-Protease Inhibitors—Part II, 48 J Label. Compd. Radiopharm., 179 (2005).*
H.R. Wiltshire, et al, The Synthesis of Labelled Forms of Saquinavir, 41 J Label. Compd. Radiopharm., 1103 (1998).*
Vermeir, M., et al., "Absorption, Metabolism, and Excretion of Darunavir, a New Protease Inhibitor, Administered Alone and with Low-Dose Ritonavir in Healthy Subjects," *DMD Fast Forward*, No. 24109, DOI:10.1124/dmd.108.024109, pp. 1-54 (Jan. 2009).
Notification of Transmittal of the International Search Report and the Written Opinion of the International Searching Authority, or The Declaration, for PCT/US09/05773, Date of Mailing: Apr. 1, 2010.
Notification of Transmittal of the International Search Report and the Written Opinion of the International Searching Authority, or The Declaration, for PCT/US2010/033206, Date of Mailing: Feb. 14, 2011.
Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).

(Continued)

*Primary Examiner* — Blessing Fubara
*Assistant Examiner* — Kauser M Akhoon
(74) *Attorney, Agent, or Firm* — Hamilton, Brook, Smith & Reynolds, P.C.

(57) ABSTRACT

This invention relates to novel compounds that are hydroxyethylamino sulfonamide derivatives and pharmaceutically acceptable salts thereof. More specifically, this invention relates to novel hydroxyethylamino sulfonamide derivatives that are derivatives of darunavir. This invention also provides compositions comprising one or more compounds of this invention and a carrier and the use of the disclosed compounds and compositions in methods of treating diseases and conditions that are beneficially treated by administering a human immunodeficiency virus (HIV) protease inhibitor, such as darunavir.

9 Claims, 1 Drawing Sheet

(56) References Cited

OTHER PUBLICATIONS

Foster, A.B., "Deuterium Isotope Effects in the Metabolism of Drugs and Xenobiotics: Implications for Drug Design," *Advances in Drug Research*, 14: 1-40 (1985).

Ghosh, A.K. et al., "Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114)," *J. Org. Chem.*, 69:7822-7829 (2004).

Ghosh, A.K. et al., "Structure-Based Design of Novel HIV-1 Protease Inhibitors to Combat Drug Resistance," *J. Med. Chem.*, 49:5252-5261 (2006).

Kushner, D.J. et al., "Pharmacological Uses and Perspectives of Heavy Water and Deuterated Compounds," *Can. J. Physiol. Pharmacol.*, 77:79-88 (1999).

Sekar, V.J. et al., "Pharmacokinetic Interaction Between Darunavir Boosted with Ritonavir and Omeprazole or Ranitidine in Human Immunodeficiency Virus-Negative Healthy Volunteers," *Antimicrobial Agents and Chemotherapy*, 51(3): 958-961 (2007).

Surleraux, D.L.N.G. et al., "Discovery and Selection of TMC114, a Next Generation HIV-1 Protease Inhibitor," *J. Med. Chem.*, 48:1813-1822 (2005).

FDA label for Prezista™* (darunavir), Tibotec, Inc., "darunavir—12.2.3 Final Labeling Text," Version 2.0, 44 pgs. (2006), downloaded on May 12, 2009 from http://www.fda.gov/cder/foi/label/2006/021976s001lbl.pdf.

Notification of Transmittal of the International Search Report and the Written Opinion of the International Searching Authority, or the Declaration; International Search Report; and Written Opinion of the International Searching Authority, International Application No. PCT/US2008/012079, Mar. 13, 2009.

Baillie, T. A., "The Use of Stable Isotopes in Pharmacological Research," *Pharmacological Reviews*, 33(2): 81-132 (1981).

Browne, T. R., "Stable Isotope Techniques in Early Drug Development: An Economic Evaluation," *J. Clin. Pharmacol.*, 38: 213-220 (1998).

Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).

Dyck, L. E., et al., "Effects of Deuterium Substitution on the Catabolism of β-Phenylethylamme: An In vivo Study," *Journal of Neurochemistry*, 46(2): 399-404 (1986).

Foster, A. B., "Deuterium Isotope Effects in Studies of Drug Metabolism," *Trends in Pharmacological Sciences*, 5: 524-527 (1984).

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," *Biomedical Mass Spectrometry*, 9(7): 269-277 (1982).

Honma S., et al., "The Metabolism of Roxatidine Acetate Hydrochloride," *Drug Metabolism and Disposition*, 15(4): 551-559 (1987).

Pieniaszek, H. J., et al., "Moricizine Bioavailability via Simultaneous, Dual, Stable Isotope Administration: Bioequivalence Implications," *J. Clin. Pharmacol*, 39: 817-825 (1999).

Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).

Vermeir, M., et al., "An Interspecies Comparison of the In vitro Metabolism of the Anti-HIV Compound TMC114," Poster PS-I-70, Microsomes and Drug Oxidation (MDO) Conference, Budapest, Hungary, held Sep. 3-7, 2006.

Wolen, R. L., "The Application of Stable Isotopes to Studies of Drug Bioavailability and Bioequivalence," *J. Clin. Pharmacol.*, 26: 419-424 (1986).

Notification Concerning Transmittal of International Preliminary Report on Patentability, Application No. PCT/US2008/012079, date of mailing May 6, 2010.

Morgan, A.J., et al., "Design and Synthesis of Deuterated Darunavir Analogs with Enhanced Pharmacokinetic Properties," ACS Fall 2011 National Meeting and Exposition: General Poster Session (341) (Aug. 28-Sep. 1, 2011), 1 pg.

"GSK Discontinues Clinical Development of Investigational Protease Inhibitor Brecanavir (640385)," Dec. 18, 2006, 1 page, downloaded on Aug. 24, 2012 from http://thebody.com/content/art39180.html.

Lalezari, J.P., et al., "Preliminary Safety and Efficacy data of Brecanavir, a Novel HIV-1 Protease Inhibitor: 24 Week Data from Study HPR10006," *Journal of Antimicrobial Chemotherapy*, 60:170-174 (2007).

Reddy, Y.S., et al., "Safety and Pharmacokinetics of Brecanavir, a Novel Human Immunodeficiency Virus Type 1 Protease Inhibitor, following Repeat Administration with and without Ritonavir in Healthy Adult Subjects," *Antimicrobial Agents and Chemotherapy*, 51(4): 1202-1208 (2007).

Notification Concerning Transmittal of International Preliminary Report on Patentability for International Application No. PCT/US2009/005773, Dated: May 5, 2011.

Office Action, U.S. Appl. No. 12/771,551, Dated: Feb. 7, 2012.

* cited by examiner

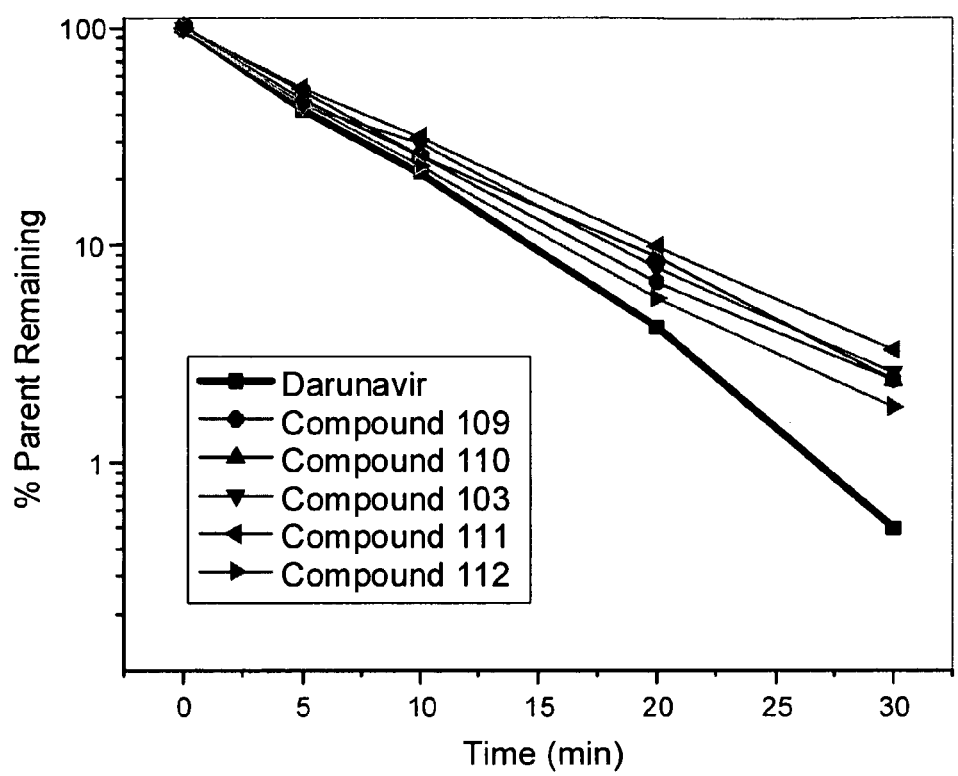

DEUTERATED DARUNAVIR

RELATED APPLICATIONS

This application is a continuation-in-part of U.S. application Ser. No. 12/290,004, filed on Oct. 24, 2008, which claims the benefit of U.S. Provisional Application No. 61/000,498, filed on Oct. 26, 2007. The entire teachings of the above applications are incorporated herein by reference.

BACKGROUND OF THE INVENTION

Darunavir, also known as Prezista™, or [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester monoethanolate, selectively inhibits the cleavage of HIV encoded Gag-Pol polyproteins in infected cells, thereby preventing the formation of mature virus particles. See FDA label for darunavir @ http://www.fda.gov/cder/foi/label/2006/021976s0011bl.pdf.

Darunavir is currently approved for treatment of HIV infection in combination with ritonavir and optionally other antiretroviral agents.

The most common adverse events experienced by patients dosed with darunavir include, but are not limited to, diarrhea, nausea, abdominal pain, constipation, headache, common cold, increased amylase, neutropenia, and nasopharyngitis. Co-administration of a darunavir/ritonavir combination is contraindicated with drugs that are highly dependent on CYP3A4 for clearance and for which elevated plasma concentrations are associated with serious and/or life-threatening events. This is because ritonavir is a potent CYP3A4 inhibitor (See FDA label for darunavir @ http://www.fda.gov/cder/foi/label/2006/021976s0011b1.pdf).

Despite the beneficial activities of darunavir, there is a continuing need for new compounds to treat the aforementioned diseases and conditions.

SUMMARY OF THE INVENTION

This invention relates to novel compounds that are hydroxyethylamino sulfonamide derivatives and pharmaceutically acceptable salts thereof. More specifically, this invention relates to novel hydroxyethylamino sulfonamide derivatives that are derivatives of darunavir. This invention also provides compositions comprising one or more compounds of this invention and a carrier and the use of the disclosed compounds and compositions in methods of treating diseases and conditions that are beneficially treated by administering a human immunodeficiency virus (HIV) protease inhibitor, such as darunavir.

BRIEF DESCRIPTION OF THE DRAWING

The FIGURE depicts the time course of metabolism of compounds of the invention as compared to darunavir in human liver microsomes.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of darunavir will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66: 15; Ganes, L Z et al., Comp Biochem Physiol Mol Integr Physiol, 1998, 119: 725.

In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 500 (7.5% deuterium incorporation) at each atom designated as deuterium a site of deuteration in said compound.

In the compounds of the invention, any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition.

The term "isotopic enrichment factor" as used herein means the ratio between the isotopic abundance and the natural abundance of that isotope. The natural abundance of deuterium is 0.015%.

In other embodiments, a compound of this invention has an isotopic enrichment factor for each designated deuterium atom of at least 1000 (15% deuterium incorporation), at least 1500 (22.5% deuterium incorporation), at least 2000 (30% deuterium incorporation), at least 2500 (37.5% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 22.5% while the other could be deuterated at 37.5%. This would be considered a compound wherein the isotopic enrichment factor is at least 1500 (22.5%).

The structural formula depicted herein may or may not indicate whether atoms at certain positions are isotopically enriched. In a most general embodiment, when a structural formula is silent with respect to whether a particular position is isotopically enriched, it is to be understood that the stable isotopes at the particular position are present at natural abundance, or, alternatively, that that particular position is isotopically enriched with one or more naturally occurring stable isotopes. In a more specific embodiment, the stable isotopes are present at natural abundance at all positions in a compound not specifically designated as being isotopically enriched.

The term "isotopologue" refers to a species that differs from a specific compound of this invention only in the isotopic composition thereof. Isotopologues can differ in the level of isotopic enrichment at one or more positions and/or in the positions(s) of isotopic enrichment.

The term "compound," as used herein, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts, solvates and hydrates of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I or II), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"US" refers to the United States of America.

"FDA" refers to Food and Drug Administration.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

The term "optionally substituted" refers to the optional replacement of one or more hydrogen atoms with another moiety. Unless otherwise specified, any hydrogen atom including a terminal hydrogen atom can be optionally replaced.

The term "halo" refers to any of —Cl, —F, —Br, or —I.

The term "carboxy" refers to —C(O)OH

The term "oxo" refers to =O.

The term "alkoxy" refers to —O-alkyl.

The term "alkylamino" refers to —NH-alkyl.

The term "dialkylamino" refers to N(alkyl)-alkyl, wherein the two alkyl moieties are the same or different.

The term "alkyl" refers to straight or branched alkyl chains of from 1 to 12 carbon atoms, unless otherwise specified. Examples of straight chained and branched alkyl groups include methyl, ethyl, n-propyl, iso-propyl, n-butyl, sec-butyl, tert-butyl, pentyl, hexyl, pentyl and octyl.

Examples of optional substituents on an alkyl group, such as a $C_{1-7}$ alkyl include halo, cyano, hydroxyl, carboxy, alkoxy, oxo, amino, alkylamino, dialkylamino, cycloheteroalkyl, aryl, and heteroaryl.

The term "cycloheteroalkyl" refers to an optionally substituted non-aromatic monocyclic, bicyclic, tricyclic, spirocyclic, or tetracyclic ring system which includes one or more heteroatoms such as nitrogen, oxygen or sulfur in at least one of the rings. Each ring can be four, five, six, seven or eight-membered. Examples include tetrahydrofuryl, tetrahydrothiophenyl, morpholino, thiomorpholino, pyrrolidinyl, piperazinyl, piperidinyl, and thiazolidinyl, along with the cyclic form of sugars. Suitable substituents on a cycloheteroalkyl can include, but are not limited to for example, alkyl, halo, cyano, hydroxyl, carboxy, alkoxy, oxo, amino, alkylamino and dialkylamino. Examples of alkyl substituted cycloheteroalkyls include, but are not limited to, 4-methylpiperazin-1-yl and 4-methylpiperidin-1-yl.

The term "aryl" refers to optionally substituted carbocyclic aromatic groups such as phenyl and naphthyl. Suitable substituents on an aryl can include, but are not limited to for example, alkyl, halo, cyano, hydroxyl, carboxy, alkoxy, amino, alkylamino and dialkylamino.

The term "heteroaryl" refers to an optionally substituted monocyclic aromatic group comprising one or more heteroatoms such as nitrogen, oxygen or sulfur in the ring, such as imidazolyl, thienyl, furyl, pyridyl, pyrimidyl, pyranyl, pyrazolyl, pyrrolyl, pyrazinyl, thiazolyl, oxazolyl, and tetrazolyl. Heteroaryl groups also include fused polycyclic aromatic ring systems in which at least one ring comprises one or more heteroatoms such as nitrogen, oxygen or sulfur. Examples include benzothienyl, benzofuryl, indolyl, quinolinyl, benzothiazole, benzoxazole, benzimidazole, quinolinyl, isoquinolinyl and isoindolyl. Suitable substituents on a heteroaryl can include, but are not limited to for example, alkyl, halo, cyano, hydroxyl, carboxy, alkoxy, amino, alkylamino and dialkylamino.

Unless otherwise specified, the term "α-amino acid" includes α-amino acids having a (D)-, (L)- or racemic (D,L) configuration. It is understood that when the variable $R^5$ is an α-amino acid, it is linked to the rest of the molecule through the carbonyl carbon directly bonded to the α-carbon of the amino acid. In accordance with the structure of Formula I, such a linkage results in the formation of an ester.

Therapeutic Compounds

The present invention provides a compound of Formula I:

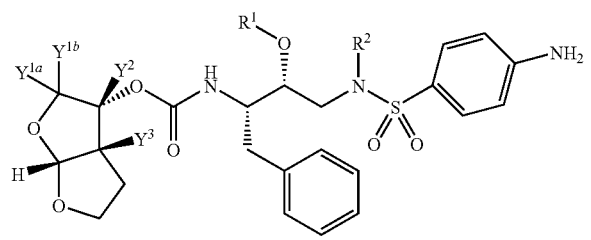

or a pharmaceutically acceptable salt thereof, wherein:
each Y is independently selected from hydrogen and deuterium;
$R^1$ is hydrogen or $-(CR^3R^4-O)_n-R^5$;
$R^2$ is an isobutyl group having 0-9 deuterium;
$R^3$ and $R^4$ are independently selected from H and $C_1$-$C_4$ alkyl;
$R^5$ is selected from an α-amino acid, $-C(O)R^6$, $-P(O)-(OM)_2$ and $-S(O)-OM$;
$R^6$ is hydrogen or an optionally substituted $C_1$-$C_7$ alkyl;
each M is H, or a cation independently selected from $Li^+$, $Na^+$, $K^+$, $Mg^{2+}$, $Ca^{2+}$, $Ba^{2+}$, and $NH_4^+$;
n is 0 or 1; and
provided that when each Y is hydrogen, then $R^2$ has 1-9 deuterium.

The term "isobutyl group having 0-9 deuterium" as used herein means a moiety of the formula $-CX_2-CX-(CX_3)_2$, where each X is independently selected from hydrogen and deuterium.

It will be readily apparent that when M is a bivalent cation, such as $Mg^{2+}$, $Ca^{2+}$, or $Ba^{2+}$, the ion will bind to a compound of Formula I in a mole ratio of 2 to 1 (Compound of Formula I: M), when $R^5=-S(O)-OM$ and in a mole ration of 1 to 1 when $R^5=-P(O)-(OM)_2$.

In a particular embodiment, $R^6$ is a $C_1$-$C_7$ alkyl optionally substituted with halo, cyano, hydroxyl, carboxy, alkoxy, oxo, amino, alkylamino, dialkylamino, cycloheteroalkyl, aryl and heteroaryl, wherein the cycloheteroalkyl, aryl and heteroaryl are each optionally further substituted.

In another embodiment, $R^5$ is selected from: an α-amino acid having an (L)-configuration and selected from serine, lysine, tyrosine, valine, glutamic acid, aspartic acid, 3-pyridylalanine and histidine; and $C(O)R^6$ wherein $R^6$ is a substituted alkyl selected from: $-CH_2OCH_3$; $-CH_2CH_2OCH_3$; $-CH_2CH_2CO_2H$; $-CH_2CH_2NH_2$; $CH_2CH_2NH-CH_3$; $-CH_2CH_2N(CH_3)_2$;

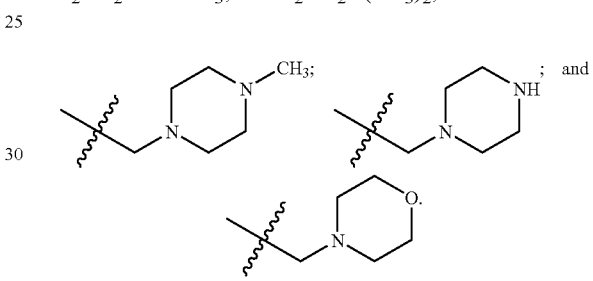

In another embodiment, M is selected from $Na^+$, $Mg^{2+}$ and $NH_4^+$.

The present invention also provides a compound of Formula II:

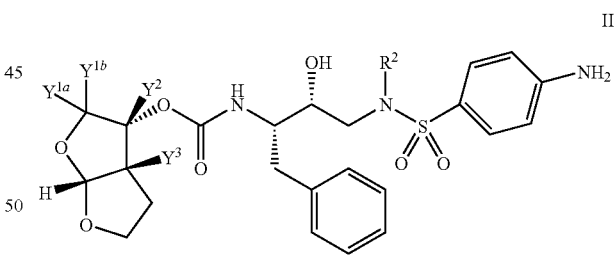

or a pharmaceutically acceptable salt thereof, wherein:
each Y is independently selected from hydrogen or deuterium; and
$R^2$ is an isobutyl group having 0-9 deuterium; and
provided that when each Y is hydrogen, then $R^2$ has 1-9 deuterium.

In one particular embodiment, $Y^{1a}$ and $Y^{1b}$ are the same. In one aspect $R^2$ is selected from $-CH_2CH(CH_3)_2$, $-CH_2CD(CH_3)_2$, $-CH_2CH(CD_3)_2$, $-CH_2CD(CD_3)_2$, and $-CD_2CD(CD_3)_2$.

In another particular embodiment, $Y^{1a}$ and $Y^{1b}$ are the same and $R^2$ is selected from $-CH_2CH(CH_3)_2$, $-CH_2CD(CH_3)_2$ and $-CH_2CD(CD_3)_2$. In one aspect of this embodiment, $Y^2$ is deuterium. In another aspect, $Y^{1a}$ and $Y^{1b}$ are both deuterium. In yet another aspect, $Y^{1a}$ and $Y^{1b}$ are both deuterium and $Y^3$ is hydrogen. In yet another aspect, $Y^{1a}$ and $Y^{1b}$ are both deuterium and $Y^3$ is deuterium. In a further aspect, $Y^{1a}$ and $Y^{1b}$ are both hydrogen. In another aspect, $Y^{1a}$ and $Y^{1b}$ are both hydrogen and $Y^3$ is hydrogen. In another aspect, $Y^{1a}$ and $Y^{1b}$ are both hydrogen and $Y^3$ is deuterium. In another aspect, $Y^3$ is deuterium. In yet another aspect, $Y^2$ is hydrogen and $Y^3$ is deuterium.

In yet another particular embodiment of Formula II, $R^2$ is selected from $-CD_2CD(CD_3)_2$ and $-CH_2CD(CD_3)_2$ and $Y^{1a}$ and $Y^{1b}$ are the same.

Specific embodiments of Formula II relate to a compound wherein:

a. $Y^{1a}$ is hydrogen, $Y^{1b}$ is hydrogen, $Y^2$ is deuterium, $Y^3$ is hydrogen, and $R^2$ is $CH_2CD(CH_3)_2$ Compound 100

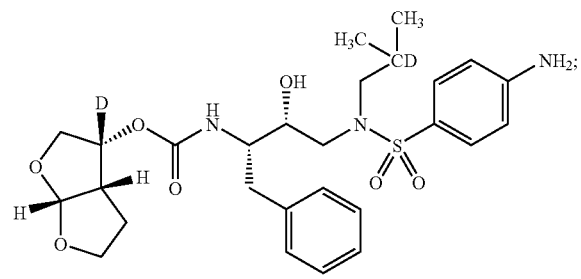

b. $Y^{1a}$ is hydrogen, $Y^{1b}$ is hydrogen, $Y^2$ is deuterium, $Y^3$ is hydrogen, and $R^2$ is $CH_2CD(CD_3)_2$ Compound 101

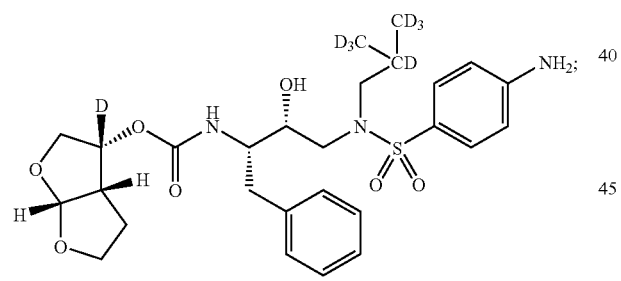

c. $Y^{1a}$ is deuterium, $Y^{1b}$ is deuterium, $Y^2$ is deuterium, $Y^3$ is hydrogen, and $R^2$ is $CH_2CD(CH_3)_2$ Compound 102

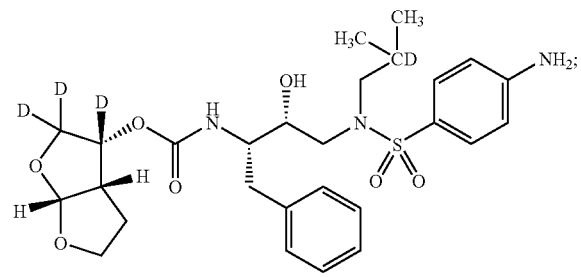

d. $Y^{1a}$ is deuterium, $Y^{1b}$ is deuterium, $Y^2$ is deuterium, $Y^3$ is hydrogen, and $R^2$ is $CH_2CD(CD_3)_2$ Compound 103

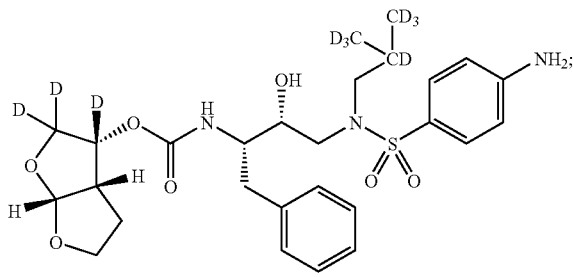

e. $Y^{1a}$ is hydrogen, $Y^{1b}$ is hydrogen, $Y^2$ is deuterium, $Y^3$ is deuterium, and $R^2$ is $CH_2CD(CH_3)_2$ Compound 104

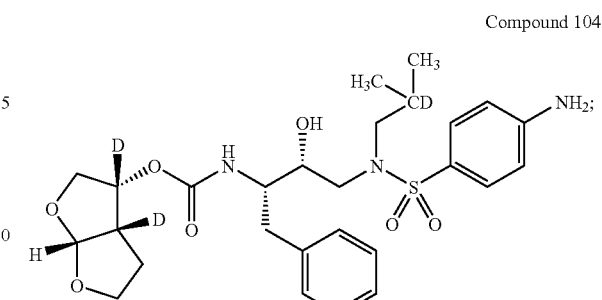

f. $Y^{1a}$ is hydrogen, $Y^{1b}$ is hydrogen, $Y^2$ is deuterium, $Y^3$ is deuterium, and $R^2$ is $CH_2CD(CD_3)_2$ Compound 105

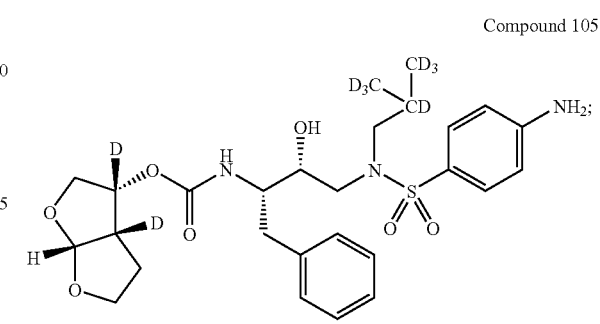

g. $Y^{1a}$ is deuterium, $Y^{1b}$ is deuterium, $Y^2$ is deuterium, $Y^3$ is deuterium, and $R^2$ is $CH_2CD(CH_3)_2$ Compound 106

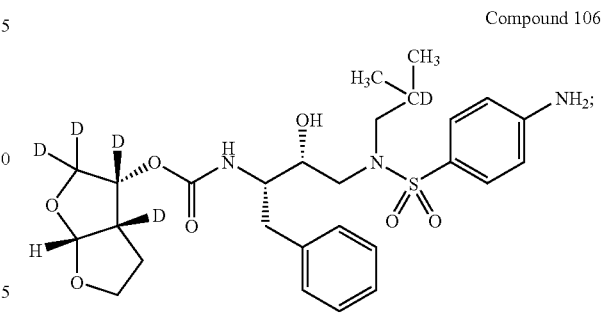

h. $Y^{1a}$ is deuterium, $Y^{1b}$ is deuterium, $Y^2$ is deuterium, $Y^3$ is deuterium, and $R^2$ is $CH_2CD(CD_3)_2$ Compound 107

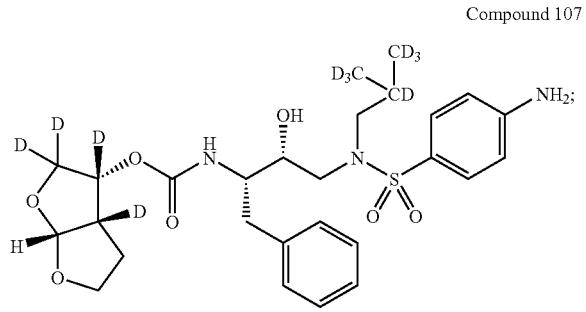

i. $Y^{1a}$ is deuterium, $Y^{1b}$ is deuterium, $Y^2$ is deuterium, $Y^3$ is deuterium, and $R^2$ is $CD_2CD(CD_3)_2$ Compound 108

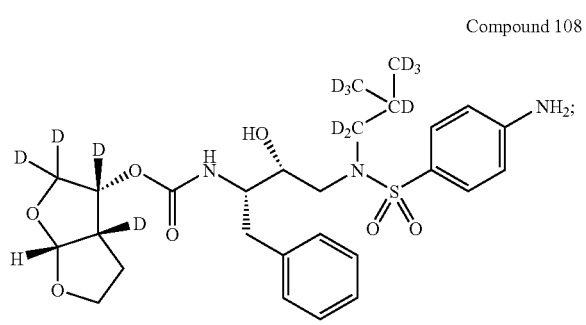

j. $Y^{1a}$ is hydrogen, $Y^{1b}$ is hydrogen, $Y^2$ is hydrogen, $Y^3$ is hydrogen, and $R^2$ is —$CD_2CD(CD_3)_2$ Compound 109 k. $Y^{1a}$ is hydrogen, $Y^{1b}$ is hydrogen, $Y^2$ is hydrogen, $Y^3$ is hydrogen, and $R^2$ is —$CH_2CD(CD_3)_2$ Compound 110

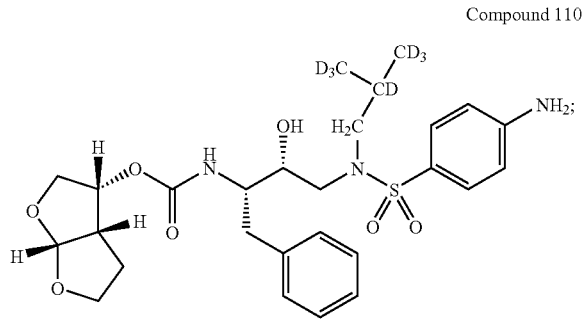

l. $Y^{1a}$ is deuterium, $Y^{1b}$ is deuterium, $Y^2$ is deuterium, $Y^3$ is hydrogen, and $R^2$ is —$CD_2CD(CD_3)_2$ Compound 111

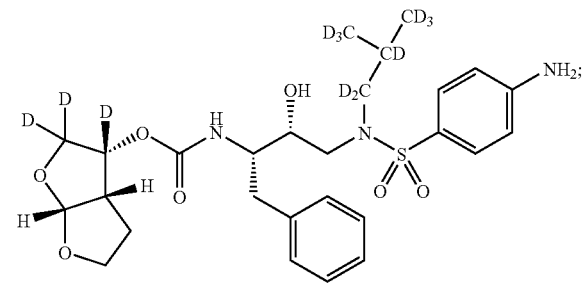

and m. $Y^{1a}$ is deuterium, $Y^{1b}$ is deuterium, $Y^2$ is deuterium, $Y^3$ is hydrogen, and $R^2$ is —$CH_2CH(CH_3)_2$ Compound 112

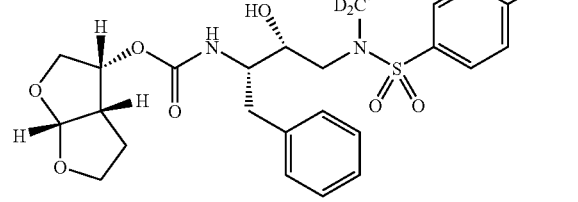

or a pharmaceutically acceptable salt of any of the foregoing.

In still another embodiment, the invention provides a compound of the Formula VII:

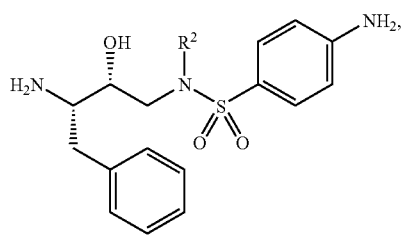

wherein $R^2$ is an isobutyl group having 1-9 deuterium, or a salt thereof.

In one aspect of this embodiment, $R^2$ is selected from —$CH_2CD(CH_3)_2$, —$CH_2CH(CD_3)_2$, —$CH_2CD(CD_3)_2$, and —$CD_2CD(CD_3)_2$. Specific examples of compounds of Formula VII include:

Compound 14

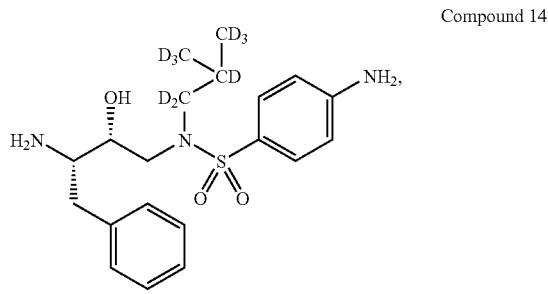

11

-continued

Compound 14b

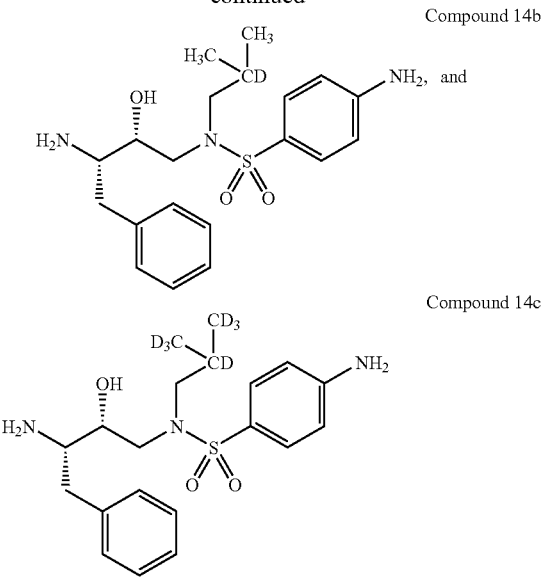

Compound 14c or a salt of any of the foregoing.

12

In another set of embodiments, any atom not designated as deuterium in any of the embodiments of Formula I, Formula II or Formula VII set forth above is present at its natural isotopic abundance.

The synthesis of compounds of Formula I, Formula II and Formula VII can be readily achieved by synthetic chemists of ordinary skill. Methods for making darunavir can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Ghosh, A K et al., J Org Chem, 2004, 69: 7822-7829; Ghosh, A K et al., J Med Chem, 2005, 48: 1813-1822; Ghosh, A K et al., J Med Chem, 2006, 49: 5252-5261; and Doan, B D et al., US Patent App Pub No US 2005/0261507. The schemes below illustrate how the compounds can be prepared.

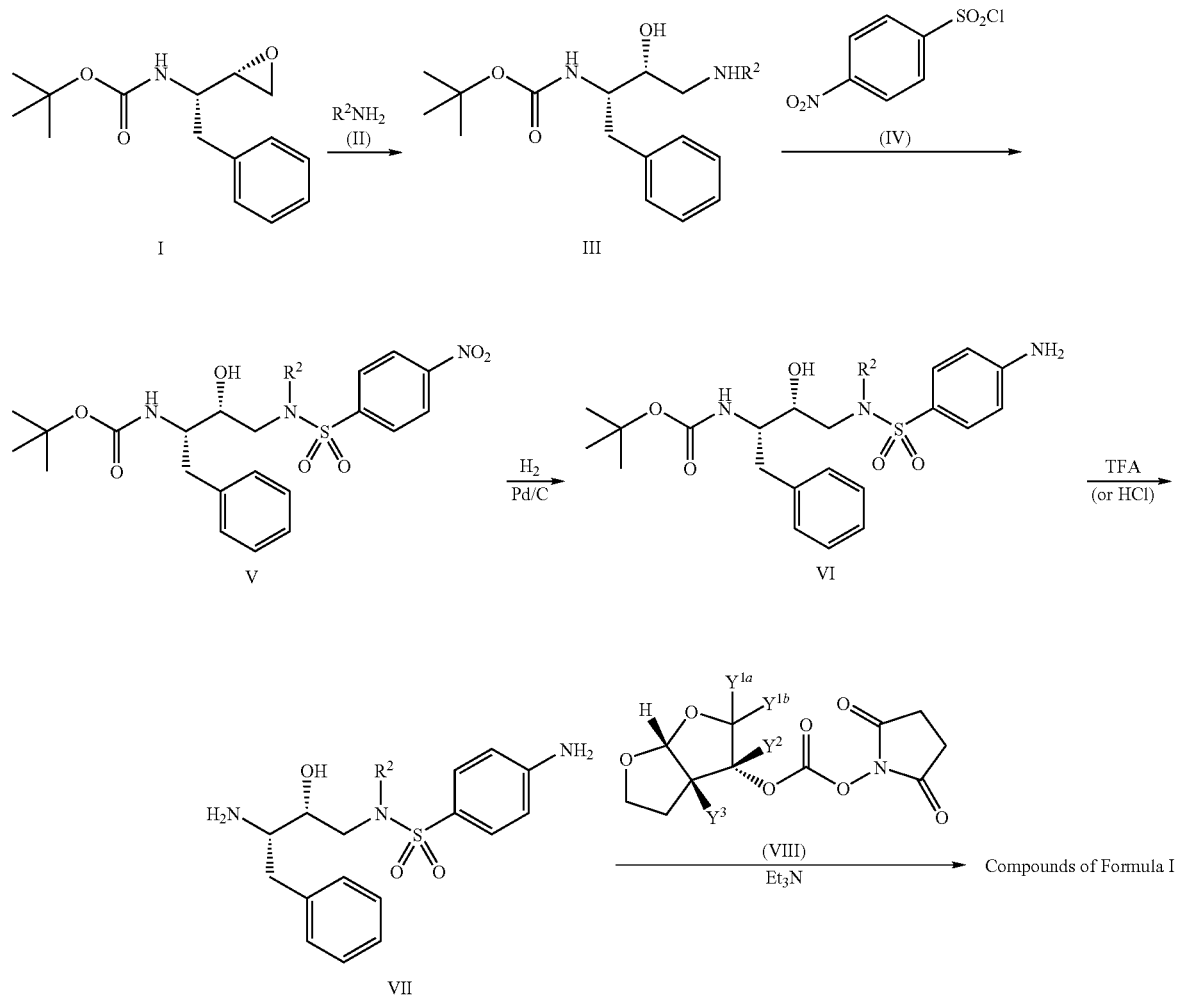

Scheme 1 above shows a general route to prepare compounds of Formula VII and conversion of the same to compounds of Formula I. Commercially available enantiopure epoxide I is opened with the substituted isobutyl amine II in hot isopropanol to provide the secondary amine III. This amine is then reacted with sulfonyl chloride IV and NaHCO$_3$ in dichloromethane to provide the sulfonamide V, which is then reduced to the aniline VI by hydrogenation over palladium on carbon. Trifluoroacetic acid treatment, or alternatively hydrochloric acid treatment, to remove the BOC group provides VII, which is then reacted with the mixed carbonate VIII and Et$_3$N in dichloromethane to provide compounds of Formula I.

Scheme 2: Preparation of Intermediate VIII.

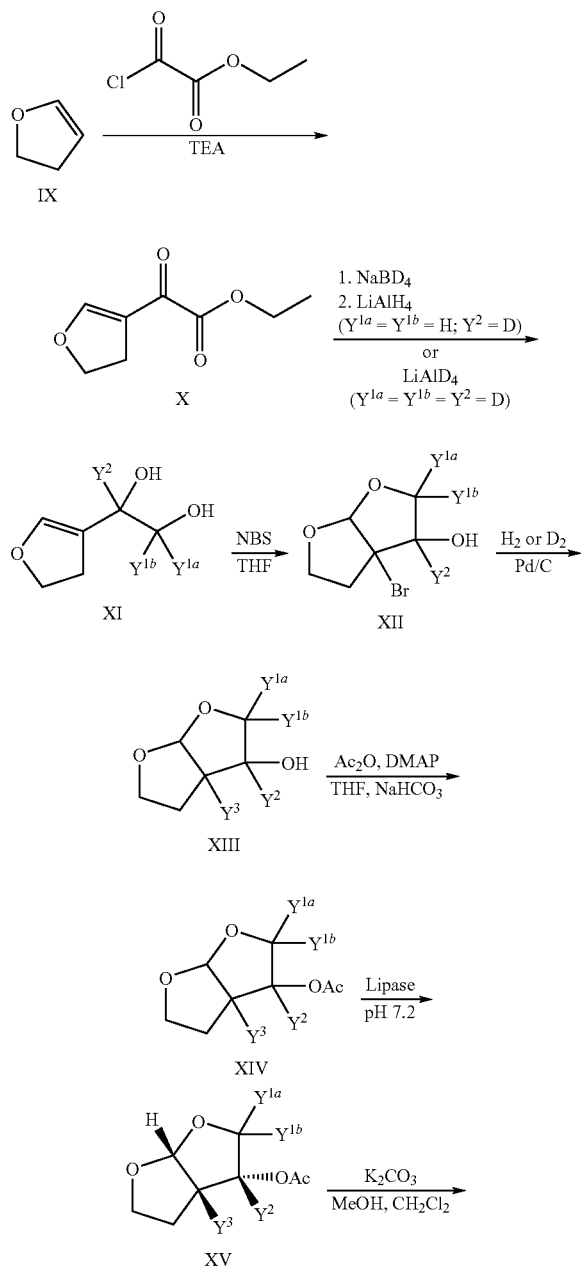

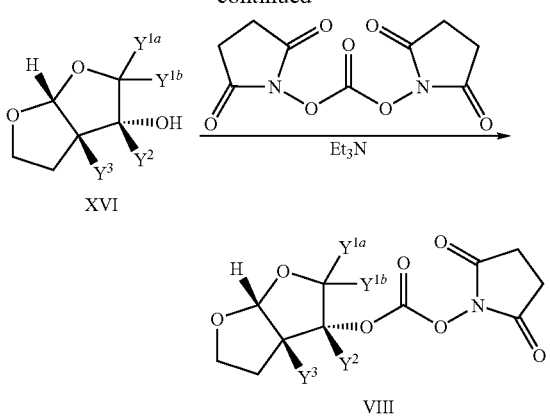

The deuterated analogs of VIII can be prepared in a manner analogous to the procedures disclosed by Doan, B D et al., US Patent App Pub No US 2005/0261507, as shown in Scheme 2. The commercially available dihydrofuran IX is reacted with commercially available ethyl chlorooxoacetate in the presence of triethylamine to provide X. Reduction of X with lithium aluminum deuteride provides the diol XI wherein all Y's are deuterium. In another route, the ketone can first be reduced with sodium borodeuteride followed by reduction with lithium aluminum hydride to provide diol XI in which only Y$^2$ is deuterium. Treatment with N-bromosuccimide provides the bicyclic compound XII, which can be reacted with hydrogen or deuterium to provide XIII in which Y$^3$ is hydrogen or deuterium. The alcohol is converted to the acetate XIV by treatment with acetic anhydride and DMAP. Treatment of XIV with lipase hydrolyzes the undesired diastereomers, which are removed in the aqueous wash to provide the enantiopure acetate XV. Hydrolysis of the acetate using potassium carbonate and methanol provides alcohol XVI, which is converted to the mixed carbonate VIII by reaction with disuccinimidyl carbonate and triethylamine in acetonitrile as described by Ghosh, A K et al., J Org Chem, 2004, 69: 7822-7829.

Scheme 3: Preparation of deuterated isobutylamine amine Intermediate II.

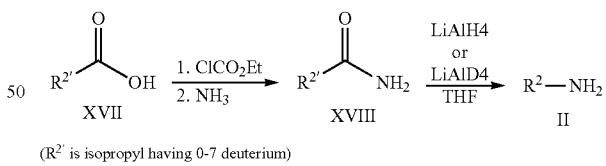

(R$^{2'}$ is isopropyl having 0-7 deuterium)

The deuterated analogs of isobutylamine II can be prepared as shown in Scheme 3. Deuterated isobutyric acid XVII is activated as the mixed anhydride with ethyl chloroformate and then reacted with ammonia to provide the amide according to the general procedure for amide formation disclosed by Alvarado, C et al., Tet Lett, 2007, 48: 603-607. Alternatively, carbonyldiimidazole may be used in place of ethyl chloroformate. The isobutyric acid amide XVIII can be readily converted to the isobutyl amine by reduction with lithium aluminum hydride or lithium aluminum deuteride in a manner analogous to the procedures disclosed in, for example, Poehler, T et al., Eur J Med Chem, 2007, 42: 175-197.

The following deuterated isobutyric acids are commercially available:

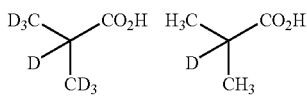

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I or Formula II (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as darunavir. Such agents include those indicated as being useful in combination with darunavir, including but not limited to, those described in WO 2003049746, WO 2005027855, and WO 2006005720.

Preferably, the second therapeutic agent is an agent useful in the treatment or prevention of a disease including, but not limited to, (HIV) infection and malaria.

In one embodiment, the second therapeutic agent is selected from other anti-retroviral agents or a pharmacokinetic enhancing agent including, but not limited to, a second HIV protease inhibitor (e.g., amprenavir, fosamprenavir, tipranavir, indinavir, saquinavir, lopinavir, ritonavir, atazanavir, darunavir or nelfinavir), a non-nucleoside reverse transcriptase inhibitor ("NNRTI") (e.g., UK-453061, GSK 2248761, etravirine (TMC125), delavirdine, efavirenz, nevirapine, or rilpivirine), a nucleoside/nucleotide reverse transcriptase inhibitor ("NRTI") (e.g., zidovudine, lamivudine, emtricitabine, tenofovir disoproxil fumarate, didanosine, stavudine, abacavir, racivir, amdoxovir, apricitabine, entecavir, adefovir or elvucitabine) a CCR5 antagonist (e.g., PF-232798; GSK 706769, enfuvirtide, maraviroc, vicriviroc, PRO140, or TNX-355), an integrase inhibitor (e.g., GSK 1349572, raltegravir, or elvitegravir), an immune based antiretroviral agent (e.g., immunitin, proleukin, remune, BAY 50-4798 or IR103), a viral maturation inhibitor (e.g., bevirimat), a cellular inhibitor (e.g., droxia or hydroxyurea), or a pharmacokinetic enhancing agent (e.g., ritonavir, GS 9350; PF-03716539) combinations of two or more of the above.

In another embodiment, the second therapeutic agent is selected from ritonavir, atazanavir, indinavir, TMC125 (etravirine), tenofovir, emtricitabine, zidovudine, lopinavir, efavirenz, fosamprenavir, tipranavir, nevirapine, lamivudine, abacavir and combinations thereof. (See label for darunavir at http://www.fda.gov/cder/foi/label/2006/021976s001_lbl.pdf and see clinical trials using darunavir at http://clinicaltrials.gov/ct/search?term=darunavir.)

In still another embodiment, the second therapeutic agent is selected from didanosine, nelfinavir, raltegravir, saquinavir, lopinavir, maraviroc, stavudine, darunavir, GSK 1349572, UK-453061, PF-03716539, etravirine, and a pharmaceutically acceptable salt of any of the foregoing, and combinations thereof.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 1 mg to about 6000 mg per treatment. In more specific embodiments the range is from about 10 to 3000 mg, or from 20 to 1200 mg, or most specifically from about 100 to 600 mg per treatment. Treatment typically is administered twice daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for darunavir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose.

The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting the activity of HIV protease in an infected cell, comprising contacting such cell with one or more compounds of Formula I or Formula II herein.

According to another embodiment, the invention provides a method of treating a disease that is beneficially treated by darunavir in a patient in need thereof comprising the step of administering to said patient an effective amount of a compound or a composition of this invention. Such diseases are well known in the art and are disclosed in, but not limited to the following patents and published applications: WO 1994004492, WO 1995006030, U.S. Pat. No. 6,335,460, and WO 2005027855. Such diseases include, but are not limited to, human immunodeficiency virus (HIV) infection and malaria.

In one particular embodiment, the method of this invention is used to treat HIV infection in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with darunavir. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or Formula II and a second therapeutic agent for treatment of the following conditions (with the particular second therapeutic agent indicated in parentheses following the indication: HIV (ritonavir, atazanavir, indinavir, TMC125 (etravirine), tenofovir, emtricitabine, zidovudine, lopinavir, efavirenz, fosamprenavir, tipranavir, nevirapine, lamivudine, and abacavir). (See clinical trials including darunavir @ http://clinicaltrials.govict/search?term=darunavir).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or Formula II alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I or Formula II for use in the treatment or prevention in a patient of a disease, disorder or symptom thereof delineated herein.

Diagnostic Methods and Kits

The present invention also provides kits for use to treat HIV infection. These kits comprise (a) a pharmaceutical composition comprising a compound of Formula I or II or a salt thereof, wherein said pharmaceutical composition is in a container; and (b) instructions describing a method of using the pharmaceutical composition to treat HIV infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

Evaluation of Metabolic Stability

SUPERSOMES™ Assay. Human cytochrome P450 3A4-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a test compound in 100 mM potassium phosphate buffer (pH 7.4) was incubated at 37° C. in triplicate. Positive controls contain 1 µM of darunavir instead of a test compound. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

EXAMPLES

Example 1

Synthesis of 4-Amino-N-((2R,3S)-3-amino-2-hydroxy-4-phenylbutyl)-N-(isobutyl-$d_9$)-benzenesulfonamide (14-$d_9$)

Scheme 4: Preparation of Intermediate 14-$d_9$.

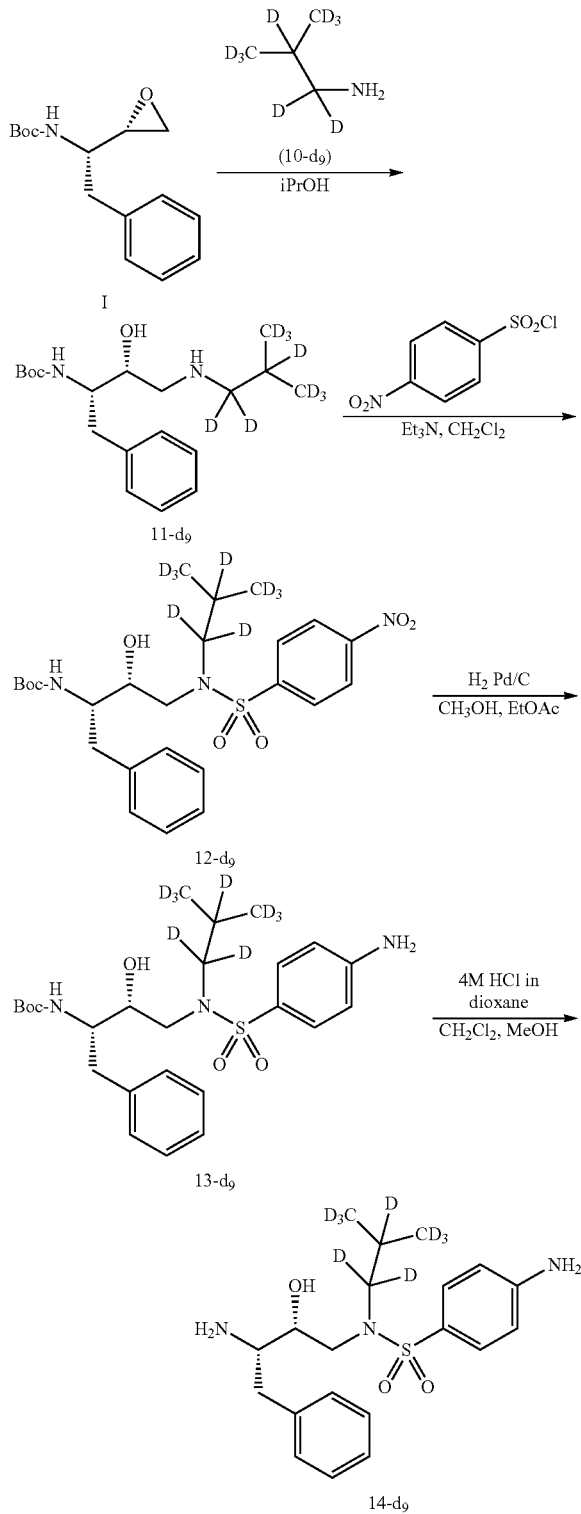

Step 1. tert-Butyl (2S,3R)-3-hydroxy-4-((isobutyl-$d_9$)-amino)-1-phenylbutan-2-ylcarbamate (11-$d_9$)

A mixture of commercially-available tent-butyl (S)-1-((S)-oxiran-2-yl)-2-phenylethyl-carbamate (I) (1.0 g, 3.8 mmol) and 2-(methylpropyl-$d_9$)-amine (10-$d_9$) (0.5 g, 6.08 mmol, CDN Isotopes, 98 atom % D) in isopropanol (30 mL) was stirred at reflux under nitrogen for 6 hours. The reaction mixture was allowed to cool overnight. The solvent was removed under reduced pressure to give crude 11-$d_9$ that was used directly in the next step without further purification.

Step 2. tert-Butyl (2S,3R)-3-hydroxy-4-(N-(isobutyl-$d_9$)-4-nitrophenylsulfonamido)-1-phenylbutan-2-ylcarbamate (12-$d_9$)

To solution of crude 11-$d_9$ (assumed 3.8 mmol) in dichloromethane (25 mL) was added triethylamine (0.46 g, 4.56 mmol, 1.2 equiv). A solution of 4-nitrobenzenesulfonyl chloride (0.84 g, 3.8 mmol, 1 equiv) in dichloromethane (5 mL) was added and the reaction mixture was stirred overnight at room temperature. The reaction mixture was diluted with dichloromethane (100 mL) and washed with water (2×60 mL), brine (60 mL), then dried over sodium sulfate and filtered. The filtrate was concentrated under reduced pressure and the crude product was purified by chromatography on silica gel (60 g), eluting with 1% ethyl acetate in dichloromethane (3 L) to give 1.28 g (64% over 2 steps) of 12-$d_9$.

Step 3. tert-Butyl (2S,3R)-4-(4-amino-N-(isobutyl-$d_2$)-phenylsulfonamido)-3-hydroxy-1-phenylbutan-2-ylcarbamate (13-$d_9$)

To a solution of 12-$d_9$ (1.26 g, 2.37 mmol) in methanol (30 mL) and ethyl acetate (30 mL) was added 20% palladium on activated carbon (50% wet, 0.20 g). The mixture was subjected to hydrogenation at 40 psi for 2.5 hours, then was filtered through a pad of Celite, washing the pad with methanol (20 mL) and ethyl acetate (20 mL). The solvents were removed under reduced pressure and the crude product was purified by chromatography on silica gel (30 g), eluting with 8% ethyl acetate in dichloromethane (4 L) to give 0.92 g (77%) of 13-$d_9$.

Step 4. 4-Amino-N-((2R,3S))-3-amino-2-hydroxy-4-phenylbutyl-N-(isobutyl-$d_9$)-benzenesulfonamide (14-$d_9$)

A solution of 13-$d_9$ (0.92 g, 1.84 mmol) in dichloromethane (20 mL) stirring at room temperature under nitrogen was treated with 4M hydrochloride solution in dioxane (1 mL, 4 mmol). Methanol (3 mL) was added and the resulting solution was stirred at room temperature under nitrogen for 3 hours. The solvents were removed under reduced pressure and the residue was dissolved in dichloromethane (20 mL). Water (10 mL) was added and the mixture was stirred in an ice-bath while 20% aqueous sodium hydroxide was slowly added to adjust the pH to 12. The phases were separated and the aqueous phase was extracted with dichloromethane (2×20 mL). The combined organic extracts were washed with brine (2×40 mL), dried over sodium sulfate and filtered. The solvent was removed under reduced pressure to give 0.71 g (96%) of 14-$d_9$ (a compound of Formula VII, wherein $R^1$ is —$CD_2$-CD-$(CD_3)_2$). $^1$H-NMR (300 MHz, CDCl$_3$): δ 2.50 (dd, $J_1$=13.4, $J_2$=9.9, 1H), 2.97 (dd, $J_1$=13.2, $J_2$=3.8, 1H), 3.12-3.31 (m, 3H), 3.72-3.77 (m, 1H), 6.69 (d, J=8.8, 2H), 7.20-7.34 (m, 5H), 7.59 (d, J=8.8, 2H). HPLC (method: 20 mm C18-RP column-gradient method 2-95% ACN+0.1% formic acid in 3.3 min with 1.7 min hold at 95% ACN; Wavelength: 254 nm): retention time: 2.52 min. MS (M+H): 401.1.

Example 2

Synthesis of (3R,3aS,6aR)-Hexahydrofuro[2,3-b]furan-3-yl(2S,3R)-4-(4-amino-N-(isobutyl-d$_9$)-phenylsulfonamido)-3-hydroxy-1-phenylbutan-2-ylcarbamate (Compound 109)

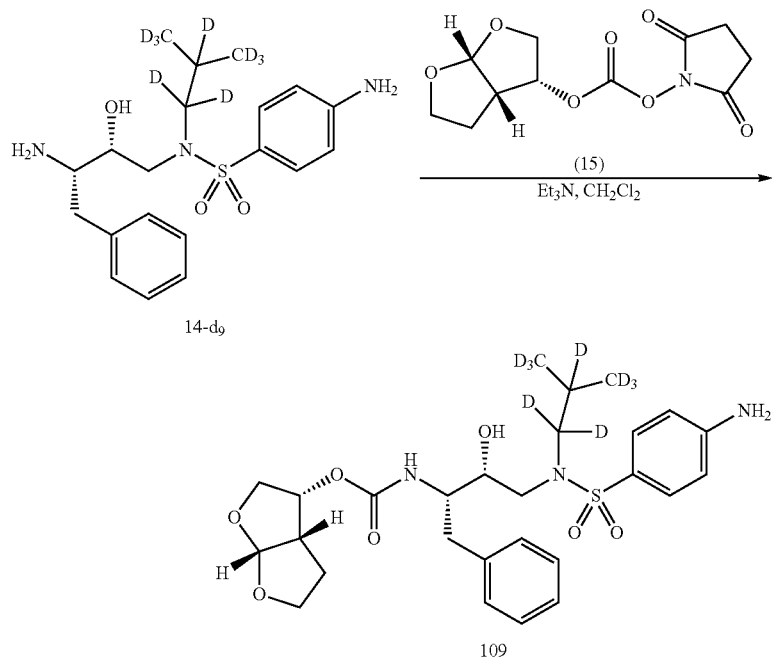

(3R,3aS,6aR)-Hexahydrofuro[2,3-b]furan-3-yl(2S,3R)-4-(4-amino-N-(isobutyl-d$_9$)-phenylsulfonamido)-3-hydroxy-1-phenylbutan-2-ylcarbamate (Compound 109). To a solution of 14-d$_9$ (0.81 g, 2.03 mmol, 1 equiv) and known 2,5-dioxopyrrolidin-1-yl-(3R,3aS,6aR)-hexahydrofuro[2,3-b]furan-3-yl carbonate (15) (0.55 g, 2.03 mmol, 1 equiv, see Ghosh, A K et al., J Org Chem, 2004, 69:7822-7829; and Canoy, W L; et al., Org. Lett., 2008, 10(6):1103-1106) in CH$_2$Cl$_2$ (50 mL) was added triethylamine (0.54 mL, 4.06 mmol, 2 equiv). The resulting solution was stirred for 4 hours, then was diluted with CH$_2$Cl$_2$ (50 mL) and washed with H$_2$O (100 mL) then brine (100 mL). The organic layer was dried over Na$_2$SO$_4$, filtered, and concentrated under reduced pressure to an orange foam. The crude material was purified using an Analogix automated chromatography system eluting with CH$_2$Cl$_2$ for 5 minutes followed by a gradient of 0-2% MeOH/CH$_2$Cl$_2$ solution over 40 minutes. Fractions containing product were concentrated under reduced pressure and dried in a vacuum oven (40° C.) for several days to give 109 as an off-white foam/solid (0.63 g, 56%) m.p. 83.3-83.8° C. $^1$H-NMR (300 MHz, CDCl$_3$): δ 1.42-1.66 (m, 2H), 2.76-2.97 (m, 3H), 3.05-3.19 (m, 2H), 3.64-3.74 (m, 3H), 3.82-3.98 (m, 4H), 4.16 (s, 2H), 4.92-5.05 (m, 2H), 5.65 (d, J=5.3, 1H), 6.69 (d, J=8.8, 2H), 7.18-7.31 (m, 5H), 7.55 (d, J=8.8, 2H). $^{13}$C-NMR (75 MHz, DMSO-d$_6$): 625.82, 35.68, 45.31, 53.71, 55.06, 69.63, 70.80, 72.82, 73.38, 109.30, 114.11, 126.05, 126.56, 128.53, 129.39, 129.52, 137.64, 150.71, 155.42. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 305 nm): retention time: 6.58 min; 99.3% purity. MS (M+H): 557.4. Elemental Analysis (C$_{27}$H$_{28}$D$_9$N$_3$O$_7$S): Calculated: C=58.26, H=6.70, N=7.55, S=5.76. Found: C=58.43, H=6.94, N=7.42, S=5.64.

Example 3

Synthesis of 2-(Methyl-d$_3$)-2,3,3,3-d$_4$-propan-1-amine (10-d$_7$)

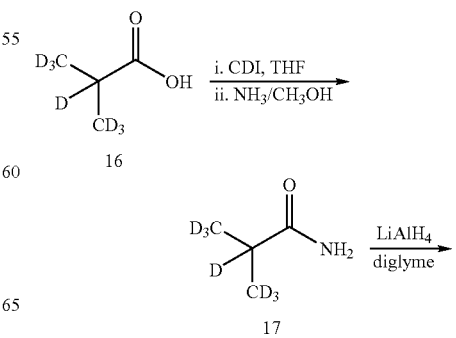

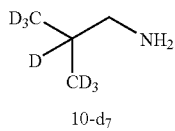

10-d₇

Step 1. (Isobutyr-d₇)-amide (17)

To a suspension of carbonyl diimidazole (CDI, 17.0 g, 111 mmol, 1.01 equiv) in THF (220 mL) was added isobutyric-d₇-acid (16) (10.0 g, 105 mmol, 1 equiv, CDN Isotopes, 98 atom % D). The reaction was stirred at room temperature for 16 hours. A solution of 7 N NH₃ in MeOH (15 mL, 105 mmol, 1 equiv) was then added dropwise, during which time the reaction temperature reached 30° C. The reaction was stirred at room temperature for 3 hours. The solvent was evaporated under reduced pressure and the residue was dissolved in THF (100 mL). 4 N HCl in dioxane (approximately 60 mL) was added and a white precipitate formed. The solids were removed by filtration and washed with THF. The filtrate was concentrated under reduced pressure and the crude product was purified by crystallization from EtOAc (30 mL) to afford 17 as a white solid (7.35 g, 76%).

Step 2. 2-(Methyl-d₃)-2,3,3,3-d₄propan-1-amine (10-d₇)

A solution of 17 (7.00 g, 74 mmol, 1 equiv) in diglyme (250 mL) was cooled to 0° C. Solid LiAlH₄ (3.11 g, 81 mmol, 1.1 equiv) was added in portions keeping the reaction temperature below 10° C. The reaction mixture was allowed to slowly warm to room temperature and was stirred overnight. The resulting turbid solution was quenched by the addition of a saturated solution of Na₂SO₄ resulting in a thick, gray suspension. The suspension was filtered through a plug of Celite, washing with additional diglyme. The filtrate was subjected to short-path distillation at atmospheric pressure. The desired product began distilling when the head temperature reached 62° C. Distillation gave 10-d₇ as a clear, colorless liquid (2.51 g, 42%). GC analysis indicated this material was 70% pure.

Example 4

Synthesis of 4-Amino-N-(2R,3S)-3-amino-2-hydroxy-4-phenylbutyl)-N-2-(methyl-d₃)-2,3,3,3-d₄-propyl-benzenesulfonamide (14-d₇)

Intermediate 14-d₇ was prepared as generally outlined in Scheme 4 above with the exception that intermediate 10-d₉ was replaced with intermediate 10-d₇. Substitution of 10-d₇ consequently resulted in intermediates 11-d₇, 12-d₇ and 13-d₇ rather than the corresponding d₉-compounds of Scheme 4. Procedures for synthesizing the d₇ compounds are provided below.

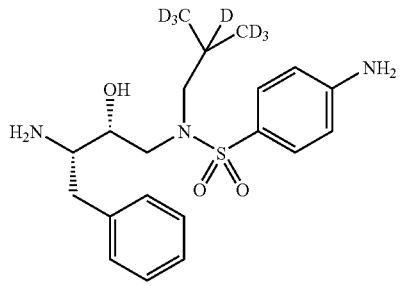

14-d₇

Step 1. tent-Butyl (2S,3R)-3-hydroxy-4-(2-(methyl-d₃)-2,3,3,3-d₄-propyl-amino)-1-phenylbutan-2-ylcarbamate (11-d₇)

To a suspension of commercially-available tert-butyl (S)-1-((S)-oxiran-2-yl)-2-phenylethylcarbamate (I)(2.60 g, 9.8 mmol, 1 equiv) in isopropanol (60 mL) was added 10-d₇ (2.0 g, 17 mmol (assumed 70% pure, 1.7 equiv). The resulting suspension was heated to reflux and stirred for 4 hours, then stirred at room temperature overnight. The solvent was then evaporated under reduced pressure to afford 11-d₇ as a white solid (3.10 g). LCMS indicated the purity of this material was 75%. The material was carried forward without further purification.

Step 2. tert-Butyl (2S,3R)-3-hydroxy-4-(N-2-(methyl-d₃)-2,3,3,3-d₄-propyl-4-nitrophenylsulfonamido)-1-phenylbutan-2-ylcarbamate (12-d₇)

To a solution of crude 11-d₇ (3.10 g, 7.4 mmol (assumed 75% purity), 1 equiv) in CH₂Cl₂ (90 mL) was added triethylamine (1.0 mL, 8.1 mmol, 1.1 equiv) followed by p-nitrobenzenesulfonyl chloride (1.62 g, 7.4 mmol, 1 equiv). The resulting solution was stirred at room temperature for 4 hours, then was diluted with CH₂Cl₂ to a volume of 200 mL. The solution was washed with H₂O (150 mL), 0.5 N HCl (150 mL), H₂O (150 mL), and saturated aqueous NaHCO₃ (150 mL). The organic layer was dried over Na₂SO₄, filtered, and concentrated under reduced pressure to afford a pale yellow solid. The crude product was purified using an Analogix automated chromatography system eluting with CH₂Cl₂ for 10 minutes followed by a gradient of 0-4% MeOH/CH₂Cl₂ over 30 minutes. Fractions containing product were concentrated under reduced pressure to give 12-d₇ as a white solid (3.03 g, 58% over two steps.)

Step 3. tert-Butyl (2S,3R)-4-(4-amino-N-2-(methyl-d₃)-2,3,3,3-d₄-propyl-phenylsulfonamido)-3-hydroxy-1-phenylbutan-2-ylcarbamate (13-d₇)

To a solution of 12-d₇ (1.40 g, 2.6 mmol, 1 equiv) in MeOH (30 mL) and EtOAc (30 mL) in a 500 mL Parr shaker bottle was added 20% Pd/C (50% wet, 0.20 g). The reaction mixture was shaken for 3 hours while maintaining a H₂ pressure of 35-40 psi. The mixture was filtered through a plug of Celite under a stream of nitrogen and the filtrate was concentrated in vacuo to afford a slightly yellow oil. The crude product was purified by silica gel chromatography eluting with 10% EtOAc/CH₂Cl₂. Fractions containing product were concentrated in vacuo to give 13-d₇ as a slightly yellow oil (1.30 g, 100%).

Step 3. 4-Amino-N-((2R,3S)-3-amino-2-hydroxy-4-phenylbutyl)-N-2-(methyl-d₃)-2,3,3,3-d₄-propyl-benzenesulfonamide (14-d₇)

4 N HCl in dioxane (8 mL, 32 mmol, 12 equiv) was added to a solution of 13-d₇ (1.30 g, 2.6 mmol, 1 equiv) in CH₂Cl₂ (25 mL). After approximately 5 minutes a white precipitate formed. MeOH (approximately 10 mL) was added until a clear solution was obtained. The mixture was then stirred at room temperature for 2 hours. The solvent was evaporated under reduced pressure and the crude material was partitioned between CH₂Cl₂ (50 mL) and H₂O (50 mL). The biphasic mixture was stirred vigorously and 10% NaOH was added until the pH reached 12. The mixture was transferred to a separatory funnel and the phases were separated. The aqueous layer was washed with an additional portion of $CH_2Cl_2$ (50 mL). The combined organic phases were washed with brine (2×200 mL), dried over $Na_2SO_4$, filtered, and concentrated under reduced pressure to give 14-$d_7$ as a slightly brown oil (0.88 g, 85%). The crude product was used without further purification.

Example 5

Synthesis of 2,5-Dioxopyrrolidin-1-yl (3R,3aS,6aR)-2,2,3-$d_3$-hexahydrofuro[2,3-b]furan-3-yl carbonate (15-$d_3$)

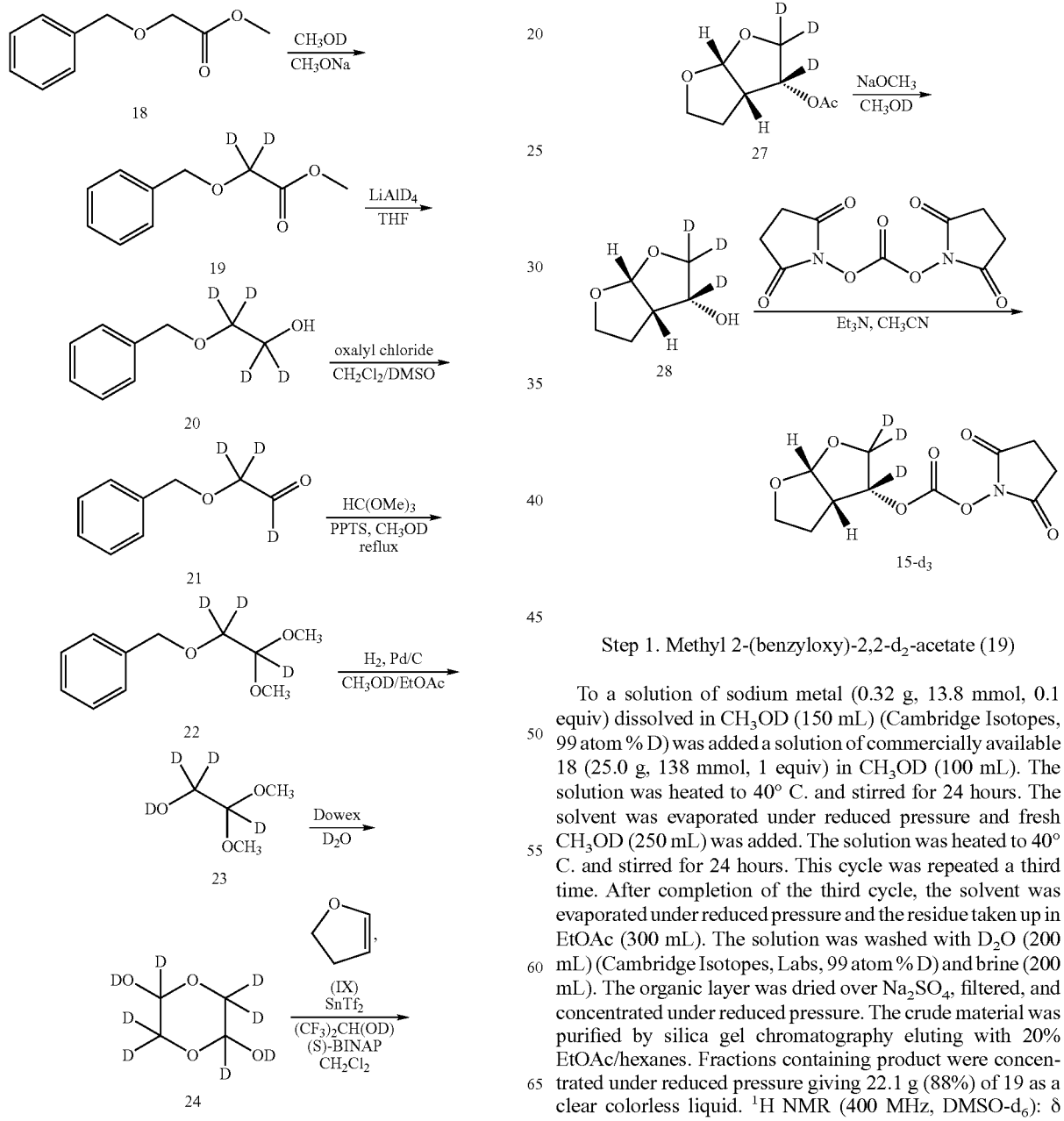

Step 1. Methyl 2-(benzyloxy)-2,2-$d_2$-acetate (19)

To a solution of sodium metal (0.32 g, 13.8 mmol, 0.1 equiv) dissolved in $CH_3OD$ (150 mL) (Cambridge Isotopes, 99 atom % D) was added a solution of commercially available 18 (25.0 g, 138 mmol, 1 equiv) in $CH_3OD$ (100 mL). The solution was heated to 40° C. and stirred for 24 hours. The solvent was evaporated under reduced pressure and fresh $CH_3OD$ (250 mL) was added. The solution was heated to 40° C. and stirred for 24 hours. This cycle was repeated a third time. After completion of the third cycle, the solvent was evaporated under reduced pressure and the residue taken up in EtOAc (300 mL). The solution was washed with $D_2O$ (200 mL) (Cambridge Isotopes, Labs, 99 atom % D) and brine (200 mL). The organic layer was dried over $Na_2SO_4$, filtered, and concentrated under reduced pressure. The crude material was purified by silica gel chromatography eluting with 20% EtOAc/hexanes. Fractions containing product were concentrated under reduced pressure giving 22.1 g (88%) of 19 as a clear colorless liquid. $^1H$ NMR (400 MHz, DMSO-$d_6$): δ 7.25-7.40 (m, 5H), 4.54 (s, 2H), 3.67 (s, 3H).

Step 2. 2-(Benzyloxy)-1,1,2,2-d$_4$-ethanol (20)

To a solution of 19 (21.0 g, 115 mmol, 1 equiv) in THF (450 mL) cooled to 4° C. in an ice-water bath was added portionwise solid lithium aluminum deuteride (5.4 g, 129 mmol, 1.1 equiv, Cambridge Isotopes, 98 atom % D). An exotherm was observed with the temperature reaching 28° C. Upon completion of the addition, the reaction was stirred 2.5 hours in the ice-water bath. The reaction was then quenched by the slow addition of 1 N HCl (150 mL) during which time the reaction temperature reached 20° C. The resulting suspension was filtered through a plug of Celite, washing with MTBE. The filtrate was transferred to a separatory funnel and extracted with MTBE (2×, 800 mL total). The combined organic layers were washed with brine (600 mL), dried over Na$_2$SO$_4$, filtered, and concentrated under reduced pressure. The crude product was purified via silica gel chromatography eluting with 2% MeOH/DCM. Fractions containing product were concentrated under reduced pressure to give 18 g (91%) of 20 as a clear colorless liquid. $^1$H NMR (400 MHz, DMSO-d$_6$): δ 7.23-7.39 (m, 5H), 4.60 (s, 1H), 4.48 (s, 2H).

Step 3. 2-(Benzyloxy)acetaldehyde-d$_3$ (21)

A solution of oxalyl chloride (7.50 mL, 33.2 mmol) in dichloromethane (17.2 mL) was stirred under nitrogen at −78° C. and a solution of dimethylsulfoxide (12.1 mL, 171 mmol) in dichloromethane (34.5 mL) was added over 5 minutes. This mixture was stirred for 20 minutes and a solution 20 (5.19 g, 33.2 mmol) in dichloromethane (17.2 mL) was added over 5 minutes. Stirring was continued for 20 minutes. Triethylamine (24.4 mL, 175 mmol) was slowly added and stirring was continued in the cold bath until the temperature reached −30° C. The cold bath was removed and 50% citric acid solution in D$_2$O was added. Stirring was continued for 5 minutes and the phases were separated. The organic layer was washed with 50% citric acid solution in D$_2$O, D$_2$O, then 1 M sodium carbonate in D$_2$O, dried over sodium sulfate and filtered. The solvent was removed on a rotary evaporator to give 21 as a brown oil which was used without further purification. $^1$H NMR (400 MHz, DMSO-d$_6$): δ 7.25-7.44 (m, 5H), 4.55 (s, 2H).

Step 4. ((2,2-dimethoxy(ethoxy-d$_3$))methyl)benzene (22)

To a mixture of 21 (10.08 g, 65.81 mmol) and trimethylorthoformate (8.64 mL, 78.9 mmol) in methanol-d (131 mL) was added PPTS (913 mg, 3.63 mmol) and the mixture stirred at reflux under nitrogen for 3 hours. The solvent was removed on a rotary evaporator. The residue was diluted with CD$_2$Cl$_2$, washed with 5% potassium carbonate solution and brine, dried over sodium sulfate, filtered and the solvent was removed on a rotary evaporator. The residue was purified via automated silica gel chromatography on an ISCO instrument (120 g silica gel, 0 to 100% EtOAc in heptanes) to give 22 (11.03 g, 84%). $^1$H NMR (400 MHz, DMSO-d$_6$): δ 7.24-7.43 (m, 5H), 4.51 (s, 2H), 3.28 (s, 6H).

Step 5. 2,2-dimethoxy(ethanol-d$_4$) (23)

To a solution of 22 (5.56 g, 27.9 mmol) in 1:1 methan(ol-d)/ethyl acetate (250 mL) was added 20% palladium on activated carbon (50% wet, purchased from Alfa Aesar, 4.73 g). The mixture was subjected to hydrogenation at 54 psi for 3 hours. The reaction mixture was filtered through Celite and the solvent was removed on a rotary evaporator to give 23 (2.83 g, 93%). $^1$H NMR (400 MHz, DMSO-d$_6$): δ 3.26 (s, 6H).

Step 6. 1,4-dioxane-2,5-diol-8(24)

A solution of 23 (5.09 g, 46.7 mmol) in D$_2$O (72 mL) was stirred with Dowex® Marathon C (235 mg) at 50° C. for 3 hours. The reaction mixture was filtered, the resin was discarded and the solvent was removed in vacuo. The crude material was purified via automated silica gel chromatography on an ISCO instrument (40 g silica gel, 0 to 100% MeCN in CH$_2$Cl$_2$) to afford 1.88 g (63%) of 24 as a clear oil. $^{13}$C NMR (2H-decoupled) analysis of the material showed that the product was very similar to the protio form of the dimer (from Aldrich). TLC Res of 24 and the protio form (10% MeOH in CH$_2$Cl$_2$) were identical. $^{13}$C NMR (400 MHz, DMSO-d$_6$): δ 104.1, 102.0, 94.1, 93.9, 89.7, 88.7, 70.6, 67.5, 65.5, 63.5, 62.5, 61.5.

Step 7. (3aS,6aR)-2,2,3-d$_3$-hexahydrofuro[2,3-b]furan-3-ol-d$_1$ (25)

A mixture of (S)-BINAP (2.89 g) and tin triflate (1.75 g) in hexafluoroisopropan(ol-d) (9.76 mL) and dichloromethane (19.5 mL) was stirred under nitrogen at room temperature for 40 minutes. Intermediate 24 (1.79 g, 13.9 mmol) in dichloromethane (3.57 mL) and hexafluoroisopropan(ol-d) (1.79 mL) was added and stirring was continued at room temperature for 40 minutes. The reaction mixture was cooled in an ice-bath and 2,3-dihydrofuran (IX) (3.18 mL, 41.8 mmol) was added by syringe such that the temperature of the reaction did not rise above 11° C. Stirring was continued in the ice-bath for 20 minutes then at room temperature overnight. The solvents were removed under reduced pressure to give crude 25. Automated silica gel chromatography on an ISCO instrument (40 g silica gel, 50 to 80% EtOAc in heptanes) afforded crude 25 (3.57 g) that was used without further purification in the next step. The enantiomeric ratio was not determined at this step, but very similar reaction conditions applied to the protio starting material have resulted in a 14% ee for the corresponding protio product. (Canoy et al. Org. Lett. 2008, 10, 1103-1106). $^1$H NMR (400 MHz, CDCl$_3$): δ 5.69 (d, J=4.8, 1H), 3.99 (dt, J=3.3, 8.1, 1H), 2.85 (m, 1H), 2.30 (ddd, J=3.0, 6.6, 10.1, 1H), 1.87 (m, 1H).

Step 8. (3aS,6aR)-2,2,3-d$_3$-hexahydrofuro[2,3-b]furan-3-yl acetate (26)

A solution of 25 (3.57 g, 26.6 mmol, assuming 100% purity) in dichloromethane (89 mL) was stirred in an ice-bath under nitrogen and triethylamine (18.6 mL, 133 mmol, 5.0 equiv) and 4-dimethylaminopyridine (0.315 g) were added. To the reaction mixture was added acetic anhydride (6.29 mL, 66.5 mmol, 2.50 equiv). The reaction mixture was allowed to warm to room temperature, stirred for 1 hour and then diluted with dichloromethane and washed with water, 1N hydrochloric acid, water, then saturated sodium bicarbonate solution. The organic layer was dried over sodium sulfate, filtered and concentrated under reduced pressure. The crude product was purified by automated silica gel chromatography on an ISCO instrument (40 g silica gel, 0 to 10% EtOAc in dichloromethane) to give 3.10 g (64% over 2 steps) of 26 as an approximately 1:1 mixture of epimers at the 3 position. $^1$H NMR (400 MHz, CDCl$_3$): δ 5.73 (d, J=5.3, 1H), 3.99 (dt, J=2.5, 8.6, 1H), 3.91 (m, 1H), 3.06 (m, 1H), 2.09 (s, 3H), 1.97-2.03 (m, 1H), 1.90 (m, 1H).

Step 9. (3R,3aS,6aR)-hexahydrofuro[2,3-b]furan-3-yl acetate-d$_3$ (27)

A mixture of 26 (0.271 g, 1.55 mmol) in pH 5.5 buffer (1.2 mL, prepared from a solution of sodium dihydrogen phosphate (5.37 g) in water (30 g) that was adjusted to pH 5.5 with 30% sodium hydroxide) was treated with Novozyme 435 (63 mg) and stirred at 40-43° C. for 1 hour. The polymer was filtered off and washed with 15% isopropanol in water. The filtrate was diluted with water and washed with dichloromethane (2×). The combined organic solutions were washed with H$_2$O (2×) and brine (1×), dried (Na$_2$SO$_4$), filtered and concentrated in vacuo. The crude product was purified via automated silica gel chromatography on an ISCO instrument (12 g silica gel, 0 to 10% EtOAc in dichloromethane) to give 0.96 mg (35%) of 27. $^1$H NMR (400 MHz, CDCl$_3$): δ 5.72 (d, J=4.8, 1H), 3.98 (dt, J=2.3, 8.1, 1H), 3.90 (m, 1H), 3.05 (m, 1H), 2.10 (s, 3H), 1.96-2.05 (m, 1H), 1.83-1.96 (m, 1H).

Step 10. (3R,3aS,6aR)-2,2,3-d$_3$-hexahydrofuro[2,3-b]furan-3-ol (28)

To a solution of 27 (96 mg, 0.548 mmol) in methan(ol-d) (1.0 mL) stirred under nitrogen at room temperature was added NaOMe (5 mg, 0.0926 mmol, 0.10 equiv). The reaction was stirred for 1 hour and then AcOH (6 µL) was added. The solvent was removed under reduced pressure and the crude product was purified via automated silica gel chromatography on an ISCO instrument (12 g silica gel, 50 to 80% EtOAc in heptanes) to give 72 mg (98%) of 28 (>99% ee by chiral GC [Column: Chiraldex G-TA, Temperature: 140° C. (isothermal), Flow rate: 1 mL/min]. $^1$H NMR (400 MHz, CDCl$_3$): δ 5.68 (d, J=5.2, 1H), 3.98 (dt, J=2.8, 8.6, 1H), 3.89 (dt, J=6.4, 9.6, 1H), 2.85 (m, 1H), 2.30 (tdd, J=2.5, 6.3, 12.9, 1H), 1.87 (m, 1H).

Step 11. 2,5-dioxopyrrolidin-1-yl(3R,3aS,6aR)-2,2,3-d$_3$-hexahydrofuro[2,3-b]furan-3-yl carbonate (15-d$_3$)

To a solution of 28 (64 mg, 0.477 mmol) in acetonitrile (0.954 mL) stirred under nitrogen at room temperature was added N,N'-disuccinylimidyl carbonate (183 mg, 0.716 mmol, 1.5 equiv). The resulting suspension was treated with triethylamine (0.133 mL, 0.954 mmol, 2.0 equiv) and the mixture stirred at room temperature overnight. The solvent was removed under reduced pressure and the residue partitioned between saturated sodium bicarbonate and ethyl acetate. Phases were separated and the aqueous phase was extracted with ethyl acetate. The combined organic extracts were washed with brine, dried over sodium sulfate, filtered and the solvent was removed under reduced pressure. The crude product was purified via automated silica gel chromatography on an ISCO instrument (12 g silica gel, 0 to 10% EtOAc in dichloromethane) to give 0.104 g (79%) of 15-d$_3$. $^1$H NMR (CDCl$_3$, 400 MHz): δ 5.75 (d, J=5.1, 1H), 4.04 (dt, J=2.0, 8.3, 1H), 3.90-3.99 (m, 1H), 3.13 (m, 1H), 2.86 (s, 4H), 2.15 (m, 1H), 1.92-2.03 (m, 1H).

Example 6

Synthesis of (3R,3aS,6aR)-Hexahydrofuro[2,3-b]furan-3-yl(2S,3R)-4-(4-amino-N-2-(methyl-d$_3$)-2,3,3,3-d$_4$-propyl-phenylsulfonamido)-3-hydroxy-1-phenylbutan-2-ylcarbamate (Compound 110)

Scheme 8. Preparation of Compound 110.

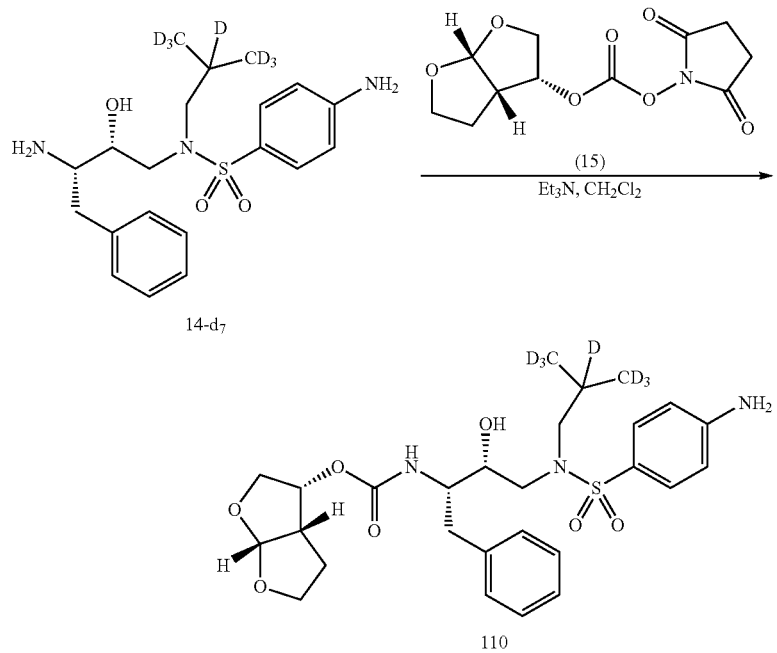

(3R,3aS,6aR)-Hexahydrofuro[2,3-b]furan-3-yl (2S,3R)-4-(4-amino-N-2-(methyl-d$_3$)-2,3,3,3-d$_4$propyl-phenylsulfonamido)-3-hydroxy-1-phenylbutan-2-ylcarbamate (Compound 110). To a solution of 14-d$_7$ (0.66 g, 1.6 mmol, 1 equiv) and 15 (0.45 g, 1.6 mmol, 1 equiv) in CH$_2$Cl$_2$ (50 mL) was added triethylamine (0.50 mL, 3.8 mmol, 2.3 equiv). The resulting solution was stirred for 4 hours at room temperature, the mixture was diluted with CH$_2$Cl$_2$ (50 mL) and washed with H$_2$O (100 mL) and brine (100 mL). The organic layer was dried over Na$_2$SO$_4$, filtered, and concentrated under reduced pressure to give a yellow oil. The crude product was purified using an Analogix automated chromatography system eluting with CH$_2$Cl$_2$ for 5 minutes followed by a gradient of 0-2% MeOH/CH$_2$Cl$_2$ solution over 40 minutes. Fractions containing product were concentrated under reduced pressure and dried in a vacuum oven (40° C.) to give 110 as an off-white foam/solid (0.47 g, 53%) m.p. 85.4-85.8° C. $^1$H-NMR (300 MHz, CDCl$_3$): δ 1.44-1.62 (m, 2H), 2.73-2.98 (m, 5H), 3.05-3.20 (m, 2H), 3.64-3.75 (m, 3H), 3.82-3.98 (m, 4H), 4.16 (s, 2H), 4.91-5.05 (m, 2H), 5.65 (d, J=5.3, 1H), 6.69 (d, J=8.8, 2H), 7.18-7.31 (m, 5H), 7.55 (d, J=8.8, 2H). $^{13}$C-NMR (75 MHz, DMSO-d$_6$): δ 25.82, 35.66, 45.31, 53.82, 55.04, 58.79, 69.63, 70.79, 72.82, 73.38, 109.29, 114.11, 126.05, 126.56, 128.53, 129.38, 129.52, 137.62, 150.69, 155.42. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 305 nm): retention time: 6.63 min; 99.6% purity. MS (M+H): 555.3. Elemental Analysis (C$_{27}$H$_{30}$D$_7$N$_3$O$_7$S): Calculated: C=58.47, H=6.72, N=7.58, S=5.78. Found: C=58.28, H=6.73, N=7.44, S=6.28.

Example 7

Synthesis of (3R,3aS,6aR)-2,2,3-d$_3$-Hexahydrofuro[2,3-b]furan-3-yl (2S,3R)-4-(4-amino-N-2-(methyl-d$_3$)-2,3,3,3-d$_4$-propyl-phenylsulfonamido)-3-hydroxy-1-phenylbutan-2-ylcarbamate (Compound 103)

Scheme 9. Preparation of Compound 103.

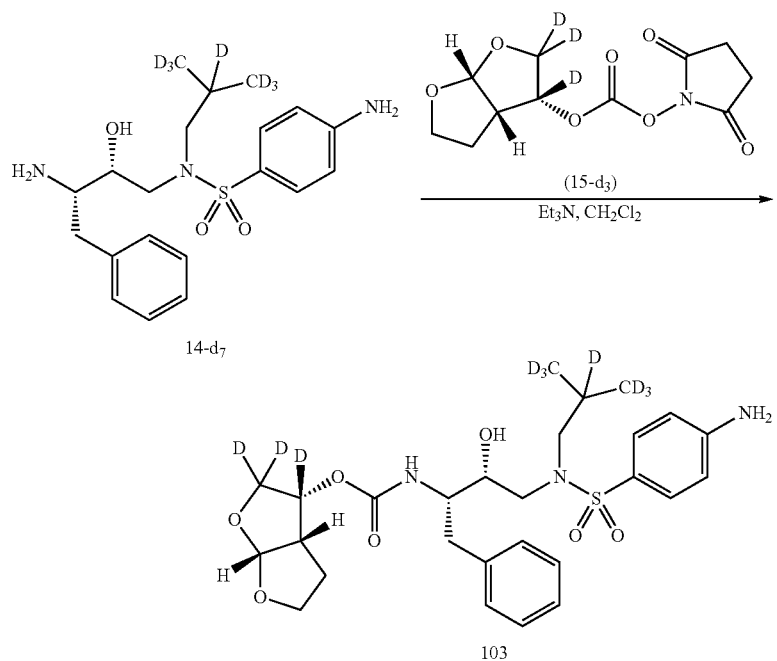

(3R,3aS,6aR)-2,2,3-d$_3$-Hexahydrofuro[2,3-b]furan-3-yl (2S,3R)-4-(4-amino-N-2-(methyl-d$_3$)-2,3,3,3-d$_4$-propyl-phenylsulfonamido)-3-hydroxy-1-phenylbutan-2-ylcarbamate (Compound 103). To a solution of 14-d$_7$ (0.086 g, 0.217 mmol) and 15-d$_3$ (0.054 g, 0.197 mmol) in dichloromethane (2.50 mL) stirred under nitrogen at room temperature was added triethylamine (0.055 mL, 0.394 mmol, 2 equiv). Stirring was continued overnight, the reaction mixture was diluted with dichloromethane and the solution was washed with water, brine, then dried over sodium sulfate and filtered. The solvent was removed under reduced pressure and the crude product was purified via automated silica gel chromatography on an ISCO instrument (12 g silica gel, 30 to 100% EtOAc in heptanes) to afford 103 (99 mg, 90%) as a white solid. 103 appears as a 77:23 mixture of rotamers in the $^1$H NMR spectrum in CDCl$_3$. Major rotamer: $^1$H NMR (400 MHz, CDCl$_3$): δ 7.55 (d, J=8.6, 2H), 7.17-7.32 (m, 5H), 6.69 (d, J=8.5, 2H), 5.64 (d, J=5.2, 1H), 4.91 (d, J=10.0, 1H), 4.20-4.07 (m, 3H), 3.93-3.76 (m, 3H), 3.76-3.64 (m, 2H), 3.15 (dd, J=9.6, 15.7, 1H), 3.01-2.85 (m, 4H), 1H), 2.85-2.69 (m, 2H), 1.71-1.58 (m, 1H), 1.50-1.40 (m, 1H). MS (M+H): 558.3.

Example 8

Synthesis of (3R,3aS,6aR)-2,2,3-d$_3$-Hexahydrofuro[2,3-b]furan-3-yl (2S,3R)-4-(4-amino-N-(isobutyl-d$_9$)-phenylsulfonamido)-3-hydroxy-1-phenylbutan-2-ylcarbamate (Compound 111)

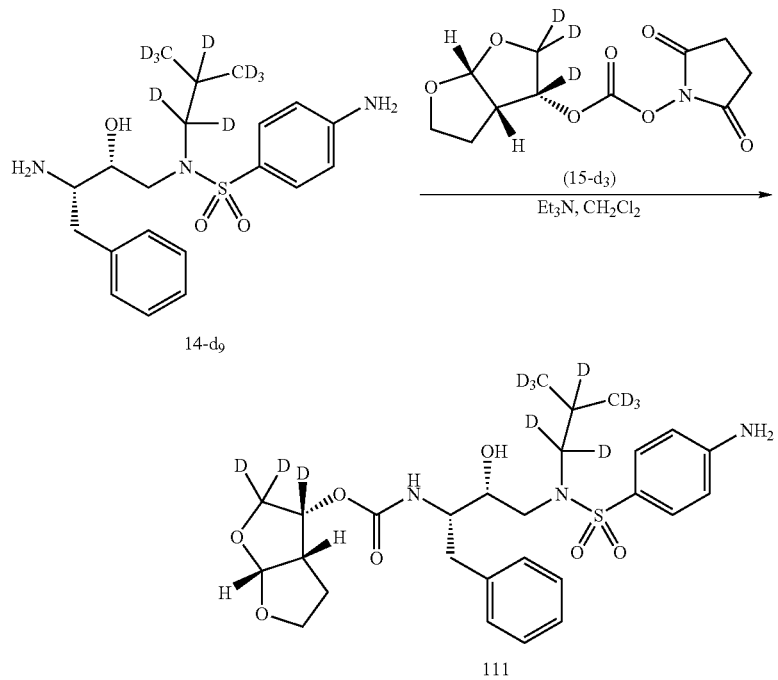

(3R,3aS,6aR)-2,2,3-d$_3$-Hexahydrofuro[2,3-b]furan-3-yl (2S,3R)-4-(4-amino-N-(isobutyl-d$_9$)-phenylsulfonamido)-3-hydroxy-1-phenylbutan-2-ylcarbamate (Compound 111)

To a solution of 14-d$_9$ (0.082 g, 0.205 mmol) and 15-d$_3$ (0.051 g, 0.186 mmol) in dichloromethane (2.36 mL) stirred under nitrogen at room temperature was added triethylamine (0.052 mL, 0.372 mmol, 2 equiv). Stirring was continued overnight, after which time an additional 0.050 mL of triethylamine were added and stirring was continued for another night. The reaction mixture was diluted with dichloromethane and the solution was washed with water, then brine, dried over sodium sulfate and filtered. The solvent was removed under reduced pressure and the crude product was purified via automated silica gel chromatography on an ISCO instrument (12 g silica gel, 30 to 100% EtOAc in heptanes) to afford 111 (95 mg, 90%) as a white solid. 111 appears as a 5:1 mixture of rotamers in the $^1$H NMR spectrum in CDCl$_3$. Major rotamer: $^1$H NMR (400 MHz, CDCl$_3$): δ 7.55 (d, J=8.8, 2H), 7.17-7.32 (m, 5H), 6.69 (d, J=8.8, 2H), 5.64 (d, J=6.1, 1H), 4.91 (d, J=8.6, 1H), 4.19-4.08 (br s, 2H), 3.92-3.79 (m, 4H), 3.76-3.64 (m, 2H), 3.14 (dd, J=9.1, 15.4, 1H), 3.07 (dd, J=4.0, 14.4, 1H), 3.03-2.85 (m, 3H), 2.80 (dd. J=9.6, 14.1, 1H), 1.69-1.58 (m, 1H), 1.50-1.41 (m, 1H). MS (M+H): 560.3.

Example 9

Synthesis of (3R,3aS,6aR)-2,2,3-d$_3$-Hexahydrofuro[2,3-b]furan-3-yl (2S,3R)-4-(4-amino-N-isobutylphenylsulfonamido)-3-hydroxy-1-phenylbutan-2-ylcarbamate (Compound 112)

Scheme 11. Preparation of Compound 112.

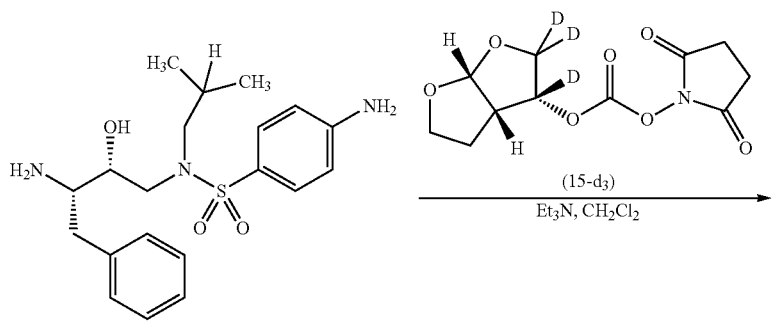

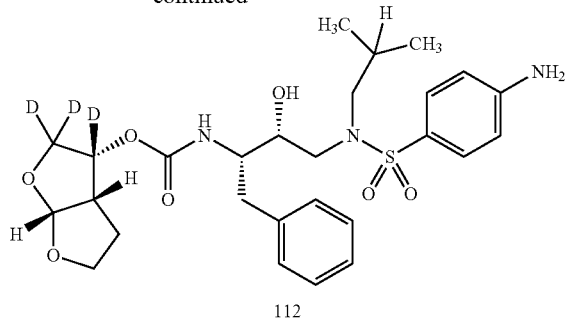

112

(3R,3aS,6aR)-2,2,3-d₃-Hexahydrofuro[2,3-b]furan-3-yl (2S,3R)-4-(4-amino-N-isobutylphenylsulfonamido)-3-hydroxy-1-phenylbutan-2-ylcarbamate (Compound 112)

To a solution of 14 (0.082 g, 0.209 mmol, prepared according to the general methods of Ghosh, A K et al., J Org Chem 2004, 69, pp. 7822-7829) and 15-d₃ (0.052 g, 0.190 mmol) in dichloromethane (2.37 mL) stirred under nitrogen at room temperature was added triethylamine (0.106 mL, 0.766 mmol, 4 equiv). Stirring was continued for 4 hours, the reaction mixture was diluted with dichloromethane and the solution was washed with water, then brine, dried over sodium sulfate and filtered. The solvent was removed under reduced pressure and the crude product was purified via automated silica gel chromatography on an ISCO instrument (12 g silica gel, 30 to 100% EtOAc in heptanes) to afford 112 (90 mg, 86%) as an off-white solid. 112 appears as a 91:9 mixture of rotamers in the ¹H NMR spectrum in CDCl₃. Major rotamer: ¹H NMR (400 MHz, CDCl₃): δ 7.55 (d, J=9.1, 2H), 7.16-7.33 (m, 5H), 6.68 (d, J=8.8, 2H), 5.65 (d, J=5.1, 1H), 4.91 (d, J=8.3, 1H), 4.15 (br s, 2H), 3.96-3.80 (m, 4H), 3.74 (d, J=1.8, 1H), 3.72-3.64 (m, 1H), 3.15 (dd, J=9.1, 15.2, 1H), 3.07 (dd, J=4.3, 14.1, 1H), 3.03-2.85 (m, 4H), 2.85-2.72 (m. J=9.6, 14.1, 2H), 1.81 (app heptet, J=6.8, 1H), 1.70-1.59 (m, 1H), 1.46 (m, 1H), 0.94 (d, J=6.8, 3H), 0.88 (d, J=7.1, 3H). MS (M+H): 551.2.

Example 10

Determination of Metabolic Stability of Test Compounds using Human Liver Microsomes Materials:

Human liver microsomes (20 mg/mL) were obtained from Xenotech, LLC (Lenexa, Kans.). β-nicotinamide adenine dinucleotide phosphate, reduced form (NADPH), magnesium chloride (MgCl₂), and dimethyl sulfoxide (DMSO) were purchased from Sigma-Aldrich.

Determination of Metabolic Stability:

7.5 mM stock solutions of test compounds (Compounds 103, 109, 110, 111, 112 and darunavir) were prepared in DMSO. The 7.5 mM stock solutions were diluted to 12.5 µM in acetonitrile (ACN). The 20 mg/mL human liver microsomes were diluted to 0.625 mg/mL in 0.1 M potassium phosphate buffer, pH 7.4, containing 3 mM MgCl₂. The diluted microsomes were added to wells of a 96-well deep-well polypropylene plate in triplicate. 10 µL of the 12.5 µM test compound was added to the microsomes and the mixture was pre-warmed for 10 minutes. Reactions were initiated by addition of pre-warmed NADPH solution. The final reaction volume was 0.5 mL and contained 0.5 mg/mL human liver microsomes, 0.25 µM test compound, and 2 mM NADPH in 0.1 M potassium phosphate buffer, pH 7.4, and 3 mM MgCl₂. The reaction mixtures were incubated at 37° C., and 50 µL, aliquots were removed at 0, 5, 10, 20, and 30 minutes and added to shallow-well 96-well plates which contained 50 µL it of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Biosystems API 4000 mass spectrometer. 7-ethoxycoumarin (1 µM) was used as a positive control. The experiment was repeated two times.

Data Analysis:

The in vitro $t_{1/2}$s for test compounds were calculated from the slopes of the linear regression of % parent remaining (ln) vs incubation time relationship. in vitro $t_{1/2}$=0.693/k, where k=–[slope of linear regression of % parent remaining (ln) vs incubation time]. Data analysis was performed using Microsoft Excel Software.

The results of these experiments are depicted in Table 1 below and in the FIGURE.

TABLE 1

Half-life of Compounds of the Invention in Human Liver Microsomes.

| Compound | $t_{1/2}$ (min) (average of two experiments) | Increase in $t_{1/2}$ over darunavir (%) |
|---|---|---|
| darunavir | 4.4 | — |
| 109 | 5.5 | 25 |
| 110 | 5.7 | 30 |
| 103 | 5.7 | 31 |
| 111 | 6.1 | 39 |
| 112 | 5.2 | 17 |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the Formula:

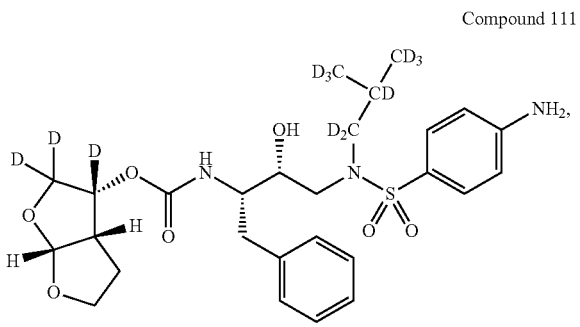

Compound 111 or a pharmaceutically acceptable salt thereof, wherein any atom not designated as deuterium is present at its natural isotopic abundance.

2. A pharmaceutical composition comprising a compound of claim 1, and a pharmaceutically acceptable carrier.

3. The composition of claim 2, comprising an additional therapeutic agent selected from a HIV protease inhibitor, a non-nucleoside reverse transcriptase inhibitor (NNRTI), a nucleoside/nucleotide reverse transcriptase inhibitor (NRTI), a CCR5 antagonist, an integrase inhibitor, an immune based antiretroviral agent, a viral maturation inhibitor, a cellular inhibitor and combinations of two or more of the above.

4. The composition of claim 2, comprising an additional therapeutic agent is selected from ritonavir, atazanavir, indinavir, TMC125, tenofovir, emtricitabine, zidovudine, lopinavir, efavirenz, fosamprenavir, tipranavir, nevirapine, lamivudine, abacavir and combinations thereof.

5. The composition of claim 2, comprising an additional therapeutic agent selected from didanosine, nelfinavir, raltegravir, saquinavir, lopinavir, maraviroc, stavudine, darunavir, GSK 1349572, UK-453061, PF-03716539, etravirine, a pharmaceutically acceptable salt of any of the foregoing, and combinations thereof.

6. A method of treating HIV infection in a patient in need thereof comprising administering to the patient an effective amount of a composition of claim 2.

7. The method of claim 6, further comprising administering to the patient in need thereof an additional therapeutic agent selected from a HIV protease inhibitor, a NNRTI, NRTI, a CCR5 antagonist, an integrase inhibitor, an immune based antiretroviral agent, a viral maturation inhibitor, a cellular inhibitor, and combinations of two or more of the above.

8. The method of claim 6, further comprising administering to the patient in need thereof an additional therapeutic agent selected from ritonavir, atazanavir, indinavir, etravirine, tenofovir, emtricitabine, zidovudine, lopinavir, efavirenz, fosamprenavir, tipranavir, nevirapine, lamivudine, abacavir and combinations thereof.

9. The method of claim 6, further comprising administering to the patient in need thereof an additional therapeutic agent selected from didanosine, nelfinavir, raltegravir, saquinavir, lopinavir, maraviroc, stavudine, darunavir, GSK 1349572, UK-453061, PF-03716539, etravirine, a pharmaceutically acceptable salt of any of the foregoing, and combinations thereof.

* * * * *